(12) United States Patent
Mizuno

(10) Patent No.: US 7,351,431 B2
(45) Date of Patent: Apr. 1, 2008

(54) FREEZE-DRIED PHARMACEUTICAL PREPARATION

(75) Inventor: Kimihiro Mizuno, Ikeda (JP)

(73) Assignee: Dainippon Sumitomo Pharma Co., Ltd., Osaka (JP)

(*) Notice: Subject to any disclaimer, the term of this patent is extended or adjusted under 35 U.S.C. 154(b) by 277 days.

(21) Appl. No.: 10/489,917

(22) PCT Filed: Sep. 19, 2002

(86) PCT No.: PCT/JP02/09607

§ 371 (c)(1),
(2), (4) Date: Apr. 30, 2004

(87) PCT Pub. No.: WO03/026642

PCT Pub. Date: Apr. 3, 2003

(65) Prior Publication Data

US 2004/0258755 A1 Dec. 23, 2004

(30) Foreign Application Priority Data

Sep. 21, 2001 (JP) .............................. 2001-290265

(51) Int. Cl.
*A61K 9/14* (2006.01)
(52) U.S. Cl. .................................................. 424/489
(58) Field of Classification Search ................ 424/400, 424/489, 617, 649
See application file for complete search history.

(56) References Cited

U.S. PATENT DOCUMENTS 4,954,522 A * 9/1990 Suzuki et al. ............... 514/492

FOREIGN PATENT DOCUMENTS

| JP | 3-255025 A | 11/1991 |
| JP | 11-315088 | * 11/1999 |
| JP | 11-315088 A | 11/1999 |

* cited by examiner

*Primary Examiner*—Sreeni Padmanabhan
*Assistant Examiner*—Konata M. George
(74) *Attorney, Agent, or Firm*—Birch, Stewart, Kolasch & Birch, LLP

(57) ABSTRACT

For clinical application of cis[((1R,2R)-1,2-cyclohexanediamine-N,N')bis($R^1$)]platinum(II) ($R^1$ is an alkanoyloxy group having 6 to 20 carbon atoms), the present invention aims at providing a formulation which prevents layer separation and changes in viscosity, shows fine suspendability, and which is easy to handle during administration. The formulation of the present invention is a lyophilized formulation for injection obtained by dissolving a cis[((1R,2R)-1,2-cyclohexanediamine-N,N')bis($R^1$)]platinum(II) in 2-methyl-2-propanol and lyophilizing this solution, which has a central particle size distribution of around 3-25 μm and a D90% value of not more than 40 μm.

1 Claim, 32 Drawing Sheets

Water content of iodine addition product of ethyl ester of fatty acids of poppyseed oil: the case of 0.6 – 0.7mg/mL Water content of iodine addition product of ethyl ester of fatty acids of poppyseed oil: the case of 0.4mg/mL (1) 20mg formulations (2) 80mg formulations (1) 20mg formulations (2) 80mg formulations 20mg formulations 80mg formulations

FIG. 17 vial X

FIG. 17 vial ◇

FREEZE-DRIED PHARMACEUTICAL PREPARATION

TECHNICAL FIELD

The present invention relates to a lyophilized formulation. More particularly, this invention relates to a lyophilized formulation comprising a cis[((1R,2R)-1,2-cyclohexanediamine-N,N')bis($R^1$)]platinum(II) (wherein $R^1$ is an alkanoyloxy group having 6 to 20 carbon atoms) as a main ingredient.

BACKGROUND ART

A suspension of a cis[((1R,2R)-1,2-cyclohexanediamine-N,N')bis($R^1$)]platinum(II), which is a platinum complex, in an iodine addition product of the ethyl ester of the fatty acids of poppyseed oil is known as a pharmaceutical agent showing a superior effect to conventional pharmaceutical agents in liver cancer, malignant lymphoma, non-small cell lung cancer, small cell lung cancer or superficial bladder cancer. Particularly, a suspension of a cis[((1R,2R)-1,2-cyclohexanediamine-N,N')bis(tetradecanoyloxy)]platinum(II) having the following structure in an iodine addition product of the ethyl ester of the fatty acids of poppyseed oil is known to show a superior effect:

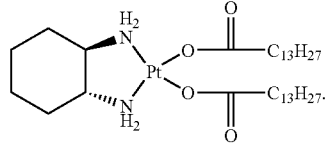

A suspension of a cis[((1R,2R)-1,2-cyclohexanediamine-N,N')bis($R^1$)]platinum(II) in an iodine addition product of the ethyl ester of the fatty acids of poppyseed oil is administered as an injection. Accordingly, a step for sterilization is necessary. As a method for sterilization, a method comprising dissolving in a solvent, followed by filtration is typical. In the case of cis[((1R,2R)-1,2-cyclohexanediamine-N,N')bis($R^1$)]platinum(II), for example, 2-methyl-2-propanol, chloroform and the like are solvents for dissolution. As a preferable solvent, 2-methyl-2-propanol is described in JP-B-2886247. However, when 2-methyl-2-propanol is used for sterile filtration and a lyophilized formulation for injection is prepared, and then the formulation is suspended in an iodine addition product of the ethyl ester of the fatty acids of poppyseed oil, problems occur in that the viscosity increases with time and the suspension separates into two layers when left standing for a long time.

DISCLOSURE OF THE INVENTION

A purpose of the present invention is to develop a formulation in which the above-mentioned problems do not occur easily, and which is stable, homogeneous and easy to handle, for clinical application of cis[((1R,2R)-1,2-cyclohexanediamine-N,N')bis($R^1$)]platinum(II).

The present inventor has conducted intensive studies in an attempt to solve the above-mentioned problems and found that by controlling the size distribution of particles obtained by dissolving an anhydrate or a hydrate of a cis[((1R,2R)-1,2-cyclohexanediamine-N,N')bis($R^1$)]platinum(II) in 2-methyl-2-propanol and lyophilizing the solution, it becomes stable and easy to handle after suspending in an iodine addition product of the ethyl ester of the fatty acids of poppyseed oil, and accomplished the present invention.

More specifically, the present inventor has found that, by controlling the particle size distribution, by dissolving a cis[((1R,2R)-1,2-cyclohexanediamine-N,N')bis($R^1$)]platinum(II) in 2-methyl-2-propanol, and adjusting the water content of the solution, or by adjusting the water content and quickly freezing the solution, the preparation after suspending in an iodine addition product of the ethyl ester of the fatty acids of poppyseed oil becomes stable, superior in suspendability and easy to handle.

Accordingly, the present invention relates to 1. a lyophilized formulation comprising a cis[((1R,2R)-1,2-cyclohexanediamine-N,N')bis($R^1$)]platinum(II), wherein $R^1$ is an alkanoyloxy group having 6 to 20 carbon atoms, as a main ingredient, which has a central particle size distribution of around 3-25 μm and a D90% value of not more than 40 μm;
2. the lyophilized formulation of 1, wherein $R^1$ is a tetradecanoyloxy group;
3. the lyophilized formulation of 1 or 2, wherein the central particle size distribution is around 5-20 μm;
4. the lyophilized formulation of any of 1 to 3, wherein the D90% value is not more than 33 μm;
5. the lyophilized formulation of any of 1 to 3, wherein the D90% value is not more than 30 μm;
6. a lyophilized formulation comprising a cis[((1R,2R)-1,2-cyclohexanediamine-N,N')bis($R^1$)]platinum(II), wherein $R^1$ is an alkanoyloxy group having 6 to 20 carbon atoms, as a main ingredient, which has a central particle size distribution of around 3-20 μm and a D90% value of not more than 40 μm;
7. the lyophilized formulation of 6, wherein $R^1$ is a tetradecanoyloxy group;
8. a lyophilized formulation comprising a cis[((1R,2R)-1,2-cyclohexanediamine-N,N')bis($R^1$)]platinum(II), wherein $R^1$ is an alkanoyloxy group having 6 to 20 carbon atoms, as a main ingredient, which has a central particle size distribution of around 3-20 μm and a D90% value of not more than 33 μm;
9. the lyophilized formulation of 8, wherein $R^1$ is a tetradecanoyloxy group;
10. a lyophilized formulation comprising a cis[((1R,2R)-1,2-cyclohexanediamine-N,N')bis(tetradecanoyloxy)]platinum(II) as a main ingredient, which has a central particle size distribution of around 3-20 μm and a D90% value of not more than 33 μm;
11. a lyophilized formulation comprising a cis[((1R,2R)-1,2-cyclohexanediamine-N,N')bis($R^1$)]platinum(II), wherein $R^1$ is an alkanoyloxy group having 6 to 20 carbon atoms, as a main ingredient, which is produced by a method comprising the following steps:
    (1) a step of dissolving a cis[((1R,2R)-1,2-cyclohexanediamine-N,N')bis($R^1$)]platinum(II) in 2-methyl-2-propanol,
    (2) a step of adjusting a water content of said solution to 1.0-6.0 mg/mL,
    (3) a step of quickly freezing said solution, and
    (4) a step of lyophilizing said frozen solution;
12. the lyophilized formulation of 11, wherein $R^1$ is a tetradecanoyloxy group;
13. the lyophilized formulation of 11 or 12, wherein freezing is done within 20 minutes;
14. the lyophilized formulation of 11 or 12, wherein freezing is done within 15 minutes;
15. the lyophilized formulation of 11 or 12, wherein freezing is done within 10 minutes;

16. the lyophilized formulation of any of 11 to 15, wherein the water content of the solution is adjusted to 1.5-5.0 mg/mL;
17. the lyophilized formulation of any of 11 to 15, wherein the water content of the solution is adjusted to 1.5-4.0 mg/mL;
18. the lyophilized formulation of any of 11 to 15, wherein the water content of the solution is adjusted to 1.5-3.0 mg/mL;
19. the lyophilized formulation of any of 11 to 18, wherein the freezing is done at −40° C.;
20. the lyophilized formulation of any of 11 to 19, which is used after suspending in an iodine addition product of the ethyl ester of the fatty acids of poppyseed oil;
21. the lyophilized formulation of any of 11 to 19, which is lyophilized in a vial;
22. a sterile lyophilized formulation comprising a cis[((1R,2R)-1,2-cyclohexanediamine-N,N')bis($R^1$)]platinum(II), wherein $R^1$ is an alkanoyloxy group having 6 to 20 carbon atoms, as a main ingredient, which is produced by a method comprising the following steps:
    (1) a step of dissolving a cis[((1R,2R)-1,2-cyclohexanediamine-N,N')bis($R^1$)]platinum(II) in 2-methyl-2-propanol,
    (2) a step of adjusting a water content of said solution to 1.0-6.0 mg/mL,
    (3) a step of sterile filtration,
    (4) a step of quickly freezing said solution, and
    (5) a step of lyophilizing said frozen solution;
23. the sterile lyophilized formulation of 22, wherein $R^1$ is a tetradecanoyloxy group;
24. the sterile lyophilized formulation of 22 or 23, wherein the freezing is done within 20 minutes;
25. the sterile lyophilized formulation of 22 or 23, wherein the freezing is done within 15 minutes;
26. the sterile lyophilized formulation of 22 or 23, wherein the freezing is done within 10 minutes;
27. the sterile lyophilized formulation of any of 22 to 26, wherein the water content of the solution is adjusted to 1.5-5.0 mg/mL;
28. the sterile lyophilized formulation of any of 22 to 26, wherein the water content of the solution is adjusted to 1.5-4.0 mg/mL;
29. the sterile lyophilized formulation of any of 22 to 26, wherein the water content of the solution is adjusted to 1.5-3.0 mg/mL;
30. the sterile lyophilized formulation of any of 22 to 29, wherein the freezing is done at −40° C.;
31. the sterile lyophilized formulation of any of 22 to 30, which is used after suspending in an iodine addition product of the ethyl ester of the fatty acids of poppyseed oil;
32. the sterile lyophilized formulation of any of 22 to 31, which is lyophilized in a vial;
33. a sterile lyophilized formulation comprising a cis[((1R,2R)-1,2-cyclohexanediamine-N,N')bis($R^1$)]platinum(II), wherein $R^1$ is an alkanoyloxy group having 6 to 20 carbon atoms, as a main ingredient, which is produced by a method comprising the following steps:
    (1) a step of dissolving a cis[((1R,2R)-1,2-cyclohexanediamine-N,N')bis($R^1$)]platinum(II) in 2-methyl-2-propanol,
    (2) a step of adjusting a water content of said solution to 1.0-6.0 mg/mL,
    (3) a step of sterile filtration,
    (4) a step of quickly freezing said solution, and
    (5) a step of lyophilizing said frozen solution under reduced pressure of 0.1-10 Torr;
34. the sterile lyophilized formulation of 33, wherein $R^1$ is a tetradecanoyloxy group;
35. the sterile lyophilized formulation of 33 or 34, wherein the freezing is done within 20 minutes;
36. the sterile lyophilized formulation of 33 or 34, wherein the freezing is done within 15 minutes;
37. the sterile lyophilized formulation of 33 or 34, wherein the freezing is done within 10 minutes;
38. the sterile lyophilized formulation of any of 33 to 37, wherein the water content of the solution is adjusted to 1.0-5.0 mg/mL;
39. the sterile lyophilized formulation of any of 33 to 38, wherein the water content of the solution is adjusted to 1.5-4.0 mg/mL;
40. the sterile lyophilized formulation of any of 33 to 39, wherein the water content of the solution is adjusted to 1.5-3.0 mg/mL;
41. the sterile lyophilized formulation of any of 33 to 40, wherein the freezing is done at −40° C.;
42. the sterile lyophilized formulation of any of 33 to 41, which is used after suspending in an iodine addition product of the ethyl ester of the fatty acids of poppyseed oil;
43. the sterile lyophilized formulation of any of 33 to 42, which is lyophilized in a vial;
44. a lyophilized formulation comprising a cis[((1R,2R)-1,2-cyclohexanediamine-N,N')bis($R^1$)]platinum(II), wherein $R^1$ is an alkanoyloxy group having 6 to 20 carbon atoms, as a main ingredient, which is produced by a method comprising the following steps:
    (1) a step of dissolving a cis[((1R,2R)-1,2-cyclohexanediamine-N,N')bis($R^1$)]platinum(II) in 2-methyl-2-propanol,
    (2) a step of adjusting a water content of said solution to 1.0-3.5 mg/mL,
    (3) a step of freezing said solution, and
    (4) a step of lyophilizing said frozen solution;
45. the lyophilized formulation of 44, wherein $R^1$ is a tetradecanoyloxy group;
46. the lyophilized formulation of 44 or 45, wherein the freezing is done within one hour;
47. the lyophilized formulation of 44 or 45, wherein the freezing is done within 40 minutes;
48. the lyophilized formulation of any of 44 to 47, wherein the water content of the solution is adjusted to 1.5-3.0 mg/mL;
49. the lyophilized formulation of any of 44 to 47, wherein the water content of the solution is adjusted to 1.5-2.5 mg/mL;
50. the lyophilized formulation of any of 44 to 47, wherein the water content of the solution is adjusted to 1.5-2.0 mg/mL;
51. the lyophilized formulation of any of 44 to 50, which is used after suspending in an iodine addition product of the ethyl ester of the fatty acids of poppyseed oil;
52. the lyophilized formulation of any of 44 to 51, which is lyophilized in a vial;
53. a lyophilized formulation comprising a cis[((1R,2R)-1,2-cyclohexanediamine-N,N')bis(tetradecanoyloxy)]platinum(II) as a main ingredient, which has a central particle size distribution of around 3-20 μm and a D90% value of not more than 33 μm, and which is produced by a method comprising the following steps:

(1) a step of dissolving a cis[((1R,2R)-1,2-cyclohexanediamine-N,N')bis(tetradecanoyloxy)]platinum(II) in 2-methyl-2-propanol,
(2) a step of adjusting a water content of said solution to 1.0-6.0 mg/mL,
(3) a step of quickly freezing said solution, and
(4) a step of lyophilizing said frozen solution under reduced pressure;

54. a sterile lyophilized formulation comprising a cis[((1R,2R)-1,2-cyclohexanediamine-N,N')bis(tetradecanoyloxy)]platinum(II) as a main ingredient, which has a central particle size distribution of around 3-20 μm and a D90% value of not more than 33 μm, and which is produced by a method comprising the following steps:
    (1) a step of dissolving a cis[((1R,2R)-1,2-cyclohexanediamine-N,N')bis(tetradecanoyloxy)]platinum(II) in 2-methyl-2-propanol,
    (2) a step of adjusting a water content of said solution to 1.0-6.0 mg/mL,
    (3) a step of sterile filtration,
    (4) a step of quickly freezing said solution, and
    (5) a step of lyophilizing said frozen solution under reduced pressure;

55. a sterile lyophilized formulation comprising a cis[((1R,2R)-1,2-cyclohexanediamine-N,N')bis(tetradecanoyloxy)]platinum(II) as a main ingredient, which has a central particle size distribution of around 3-20 μm and a D90% value of not more than 33 μm, and which is produced by a method comprising the following steps:
    (1) a step of dissolving a cis[((1R,2R)-1,2-cyclohexanediamine-N,N')bis(tetradecanoyloxy)]platinum(II) in 2-methyl-2-propanol,
    (2) a step of adjusting a water content of said solution to 1.0-6.0 mg/mL,
    (3) a step of sterile filtration,
    (4) a step of quickly freezing said solution, and
    (5) a step of lyophilizing said frozen solution under reduced pressure of 0.1-10 Torr;

56. the sterile lyophilized formulation of any of 53 to 55, wherein the freezing is done within 20 minutes;
57. the sterile lyophilized formulation of any of 53 to 55, wherein the freezing is done within 15 minutes;
58. the sterile lyophilized formulation of any of 53 to 55, wherein the freezing is done within 10 minutes;
59. the sterile lyophilized formulation of any of 53 to 58, wherein the water content of the solution is adjusted to 1.0-5.0 mg/mL;
60. the sterile lyophilized formulation of any of 53 to 58, wherein the water content of the solution is adjusted to 1.5-4.0 mg/mL;
61. the sterile lyophilized formulation of any of 53 to 58, wherein the water content of the solution is adjusted to 1.5-3.0 mg/mL;
62. the sterile lyophilized formulation of any of 53 to 61, wherein the freezing is done at −40° C.;
63. a lyophilized formulation comprising a cis[((1R,2R)-1,2-cyclohexanediamine-N,N')bis(tetradecanoyloxy)]platinum(II) as a main ingredient, which has a central particle size distribution of around 3-20 μm and a D90% value of not more than 33 μm, and which is produced by a method comprising the following steps:
    (1) a step of dissolving a cis[((1R,2R)-1,2-cyclohexanediamine-N,N')bis(tetradecanoyloxy)]platinum(II) in 2-methyl-2-propanol,
    (2) a step of adjusting a water content of said solution to 1.0-3.5 mg/mL,
    (3) a step of freezing said solution, and
    (4) a step of lyophilizing said frozen solution;

and the like.

BRIEF DESCRIPTION OF THE DRAWINGS

FIG. 7B is an output of the particles (spherical) of the lyophilized formulation having a water content of the drug solution before freezing of 3.0 mg/mL, FIG. 7C is an output of the particles (needle) of the lyophilized formulation having a water content of the drug solution before freezing of 5.0 mg/mL and FIG. 7D is an output of the particles (amorphous) of the lyophilized formulation having a water content of the drug solution before freezing of 0.5 mg/mL.

FIGS. 10A-F are outputs of differential interference microscopic observation of the particles of the lyophilized formulations in Experimental Example 3, wherein FIG. 10A is an output of the particles of the lyophilized formulation (20 mg formulation, spherical), FIG. 10B is an output of the particles of the lyophilized formulation (20 mg formulation, fiber), FIG. 10C is an output of the particles of the lyophilized formulation (20 mg formulation, microfiber), FIG. 10D is an output of the particles of the lyophilized formulation (20 mg formulation, spherical), FIG. 10E is an output of the particles of the lyophilized formulation (80 mg formulation, spherical) and FIG. 10F is an output of the particles of the lyophilized formulation (80 mg formulation, microfiber).

DETAILED DESCRIPTION OF THE INVENTION

Figure 1A:
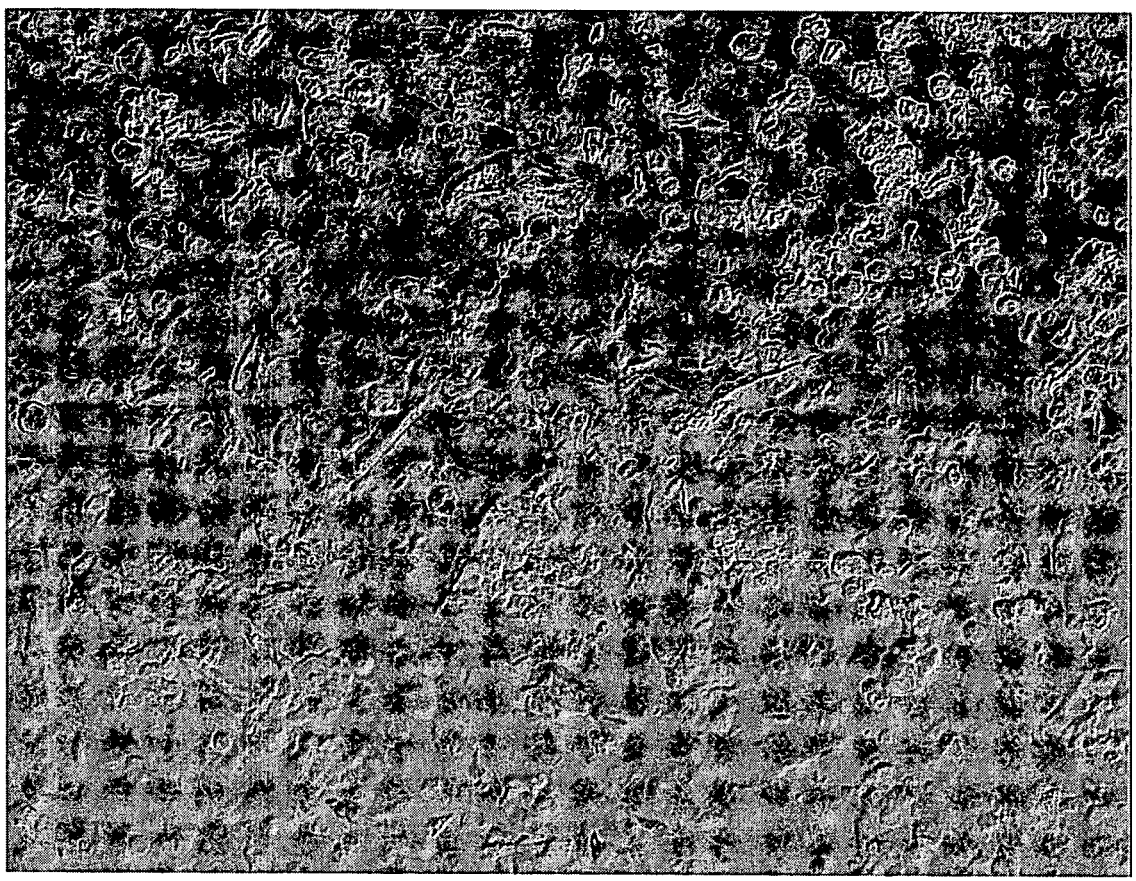
FIG. 1A is an output of differential interference microscopic observation of the particles of the lyophilized formulation of Formulation No. 1 (Experimental Example 1)

The present invention is characterized in that the particle size distribution of the main ingredient of a lyophilized formulation is controlled within a predetermined range. This has a consequence that a stable injection easy to handle can be produced, wherein suspendability is fine, layer separation does not occur easily, the viscosity does not change easily and the like. That is, for a stable injection to be obtained, the particle size distribution of the lyophilized formulation preferably is a central particle size distribution of around 3-25 μm, more preferably around 3-20 μm, particularly preferably around 5-20 μm. Here, for example, the "central particle size distribution of around 3-25 μm" means the highest frequency particle size fraction (range of particle size where a particle size is highest in the distribution frequency) is present), namely, that the peak of a particle size distribution profile) is in the range of 3-25 μm. In addition, it is preferable that the D90% value be not more than 40 μm, it is more preferable that the D90% value be not more than 33 μm, the D75% value be not more than 22 μm and the D50% value be not more than 15 μm, and it is particularly preferable that the D90% value be not more than 30 μm, the D75% value be not more than 20 μm and the D50% value be not more than 13 μm. The methods for controlling the particle size distribution of a lyophilized formulation to these ranges are to be described later.

The index "D value" of the particle size distribution means as it is generally used in the pertinent field. Namely, by the "Dx % value is p μm" is meant that the number of x % particles of the whole particles are not more than p μm and the number of (100–x) % particles are greater than p μm. The "size" of a particle is what is called a sphere equivalent diameter, which shows a diffraction behavior equivalent to a standard spherical particle having the same size in, for example, one measurement with a laser diffractometer.

The lyophilized formulation of the present invention comprises, as a main ingredient, a cis[((1R,2R)-1,2-cyclohexanediamine-N,N')bis($R^1$)]platinum(II) having the abovementioned predetermined particle size distribution. As used herein, by "as a main ingredient" is meant that the aforementioned compound is contained in a lyophilized formulation in a proportion of not less than 95 weight % (preferably 97-100 weight %, particularly preferably 100 weight %).

$R^1$ in the cis[((1R,2R)-1,2-cyclohexanediamine-N,N')bis($R^1$)]platinum(II) to be used in the present invention is an alkanoyloxy group having 6 to 20 carbon atoms, such as hexanoyloxy, heptanoyloxy, octanoyloxy, nonanoyloxy, decanoyloxy, undecanoyloxy, dodecanoyloxy, tridecanoyloxy, tetradecanoyloxy, pentadecanoyloxy, hexadecanoyloxy, heptadecanoyloxy, octadecanoyloxy, nonadecanoyloxy, icosanoyloxy or the like. Preferable alkanoyloxy group includes an alkanoyloxy group having 10 to 16 carbon atoms, which is, for example, decanoyloxy, undecanoyloxy, dodecanoyloxy, tridecanoyloxy, tetradecanoyloxy, pentadecanoyloxy, hexadecanoyloxy or the like. More preferable alkanoyloxy group includes an alkanoyloxy group having 13 to 15 carbon atoms, which is, for example, tridecanoyloxy, tetradecanoyloxy, pentadecanoyloxy or the like. A particularly preferable alkanoyloxy group is tetradecanoyloxy or the like.

The cis[((1R,2R)-1,2-cyclohexanediamine-N,N')bis($R^1$)]platinum(II) to be used in the present invention may be an anhydrate or a hydrate. These are collectively referred to as an "active ingredient" in the following.

The lyophilized formulation for injection of the present invention can be produced as in the following.

Manufacturing Method 1

(1) Dissolution Step cis[((1R,2R)-1,2-Cyclohexanediamine-N,N')bis($R^1$)]platinum(II) is added to 2-methyl-2-propanol and pulverized and suspended at room temperature. To the suspension is added 2-methyl-2-propanol to allow for dissolution. Alternatively, 2-methyl-2-propanol is added to cis[((1R,2R)-1,2-cyclohexanediamine-N,N')bis($R^1$)]platinum(II) and ultrasonication and the like are applied for 10 min to 1 hr at 30° C. to 50° C. to allow for dissolution. The amount of 2-methyl-2-propanol need only to be not less than an amount in which cis[((1R,2R)-1,2-cyclohexanediamine-N,N')bis($R^1$)]platinum(II) dissolves.

(2) Water Content Adjusting Step

The water content of a solution of cis[((1R,2R)-1,2-cyclohexanediamine-N,N')bis($R^1$)]platinum(II) in 2-methyl- 2-propanol is measured using a Karl-Fischer moisture meter and the like. Based on the measured water content, the water content of the solution is adjusted. The water content varies depending on the freezing method (to be mentioned later) of the solution. When the solution is to be frozen quickly, the content is selected from the range of 1.0-6.0 mg/mL, preferably 1.5-5.0 mg/mL, more preferably 1.5-4.0 mg/mL, still more preferably 1.5-3.5 mg/mL, and yet more preferably 1.5-3.0 mg/mL. When the solution is not to be frozen quickly, the content is selected from the range of 1.5-3.5 mg/mL, preferably 1.5-3.0 mg/mL, more preferably 1.5-2.5 mg/mL, and still more preferably 1.5-2.0 mg/mL.

(3) Filtration Step

A solution is subjected to sterile filtration using a filter for sterilization.

(4) Filling Step

A predetermined amount of the sterilized solution is filled in a vial.

(5) Freezing Step

The shelf temperature of a lyophilizer is set to a temperature not higher than the freezing temperature of the solution and the vial is placed thereon to allow for freezing. Alternatively, the temperature is set to a temperature not lower than the freezing temperature of the solution and the vial is placed thereon and frozen by lowering the temperature to a freezing temperature of the solution at a predetermined cooling rate. The steps (4) and (5) are preferably performed under the condition of preventing moisture absorption. The freezing is preferably done quickly. In the present specification, by "freezing is done quickly" is meant that the solution is frozen within 20 minutes. However, freezing is more preferably done within 15 minutes, further within 10 minutes, particularly preferably within 2-10 minutes.

(6) Freeze-drying Step

The inside of a lyophilizer is depressurized to allow for lyophilization.

Manufacturing Method 2

(1) Dissolution Step cis[((1R,2R)-1,2-Cyclohexanediamine-N,N')bis($R^1$)]platinum(II) monohydrate is added to 2-methyl-2-propanol and pulverized and suspended at room temperature. The amount of 2-methyl-2-propanol is selected from the range of 12.5 ml ±5% to 1 g (based on anhydrate) of a cis[((1R,2R)-1,2-cyclohexanediamine-N,N')bis($R^1$)]platinum(II). To the suspension is added 2-methyl-2-propanol such that 2-methyl-2-propanol is 250 mL per 1 g (based on anhydrate) of cis[((1R,2R)-1,2-cyclohexanediamine-N,N')bis($R^1$)]platinum(II). The temperature is adjusted to about 30-40° C. and cis[((1R,2R)-1,2-cyclohexanediamine-N,N')bis($R^1$)]platinum(II) monohydrate is dissolved. 2-Methyl-2-propanol to be used for this step may be any as long as it has a quality usable for pharmaceutical production. Preferably, distilled 2-methyl-2-propanol is used.

(2) Water Content Adjusting Step

The water content of a solution of cis[((1R,2R)-1,2-cyclohexanediamine-N,N')bis($R^1$)]platinum(II) in 2-methyl-2-propanol is measured using a Karl-Fischer moisture meter and the like. Based on the measured water content, the water content of the solution is adjusted to about 1.0-about 5.0 mg/mL by adding distilled water. The distilled water to be used in this step is preferably sterilized, and distilled water for injection. Steps (1) and (2) are preferably performed in an isolator.

(3) Filtration Step

The solution is pressurized with nitrogen (pressure: generally not more than 1.5 kgf/cm$^2$, preferably 0.1-0.9 kgf/cm$^2$), and subjected to sterile filtration using a filter having a pore size of about 0.2 μm. The filter to be used is preferably one usable for organic solvents.

(4) Filling Step

A predetermined amount of the sterilized solution is filled in a vial. In the case of a 20 mg formulation, for example, 5 mL is filled; in the case of a 70 mg formulation, 17.5 mL is filled; and in the case of a 80 mg formulation, 20 mL is filled.

(5) Freezing Step

The shelf temperature of a lyophilizer is set to −40° C. and a halfway stoppered vial is placed thereon. The solution in the vial is frozen within 20 minutes, preferably within 15 minutes (more preferably 2-10 minutes). The steps (4) and (5) are preferably performed under a low moisture environment (environment temperature: 28-35° C., relative humidity: 5-40%) under the condition of preventing moisture absorption.

(6) Lyophilizing Step

The inside of a lyophilizer is depressurized to allow for lyophilization. The lyophilization is preferably performed as follows.

Primary lyophilizing conditions: shelf temperature
−20° C. to 10° C., degree of vacuum 0.1-5 Torr
Secondary lyophilizing conditions: shelf temperature
40° C. to 60° C., degree of vacuum 0.1-1 Torr.

The dose of the lyophilized formulation for injection of the present invention is generally 1-500 mg/day as an active ingredient for an adult. The administration method is, for example, topical arterial injection, and is particularly preferably hepatic artery catheterization.

The lyophilized formulation for injection of the present invention can be administered in the form of a suspension in an iodine addition product of the ethyl ester of the fatty acids of poppyseed oil and the like. In this case, the concentration of the active ingredient is desirably 1-100 mg/mL. It has been clarified that, when the lyophilized formulation produced by the aforementioned method is suspended in an iodine addition product of the ethyl ester of the fatty acids of poppyseed oil, increased viscosity and layer separation of suspension with the lapse of time can be prevented (see Experimental Examples).

EXAMPLES

The present invention is explained in detail by referring to Examples, which are not to be construed as limitative.

Experimental Example 1

2-Methyl-2-propanol (1000 ml) was added to cis[((1R,2R)-1,2-cyclohexanediamine-N,N')bis(tetradecanoyloxy)]platinum(II) monohydrate (4 g) and the mixture was ultrasonicated for 30 min. The mixture was stirred at 30-40° C. to allow for dissolution (in Experimental Example 2 and the following, this solution is referred to as a "drug solution"). This solution was passed through a filter (pore size 0.22 μm) for sterilization. This solution was filled in a vial by 5 mL. The vial was placed on a shelf set at 30° C. and gradually cooled to −40° C. over about 2 hr to allow for freezing. It was lyophilized to give lyophilization formulations for injection (20 mg) having various particle sizes (to be measured in the following "Experimental Example 1-1").

Experimental Example 1-1

Figure 1B:
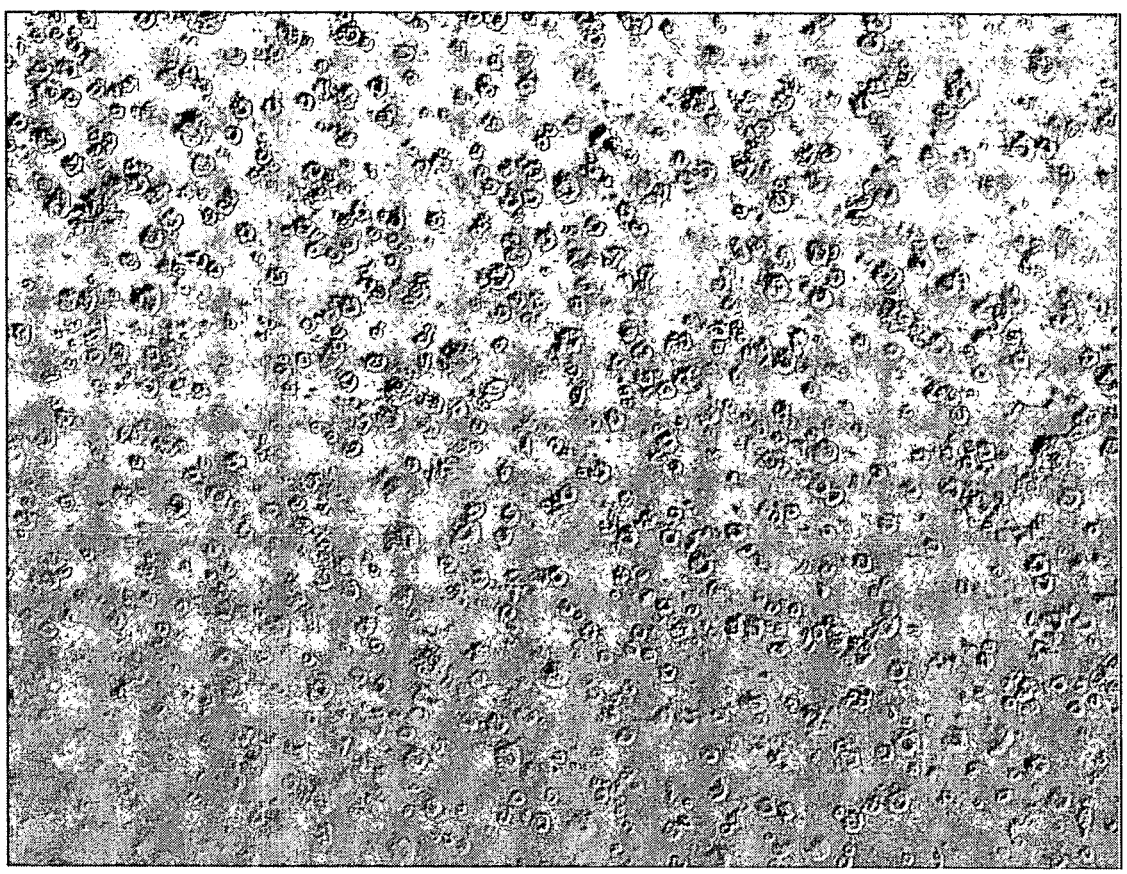
FIG. 1B is an output of differential interference microscopic observation of the particles of the lyophilized formulation of Formulation No. 5 (Experimental Example 1).
Figure 2:
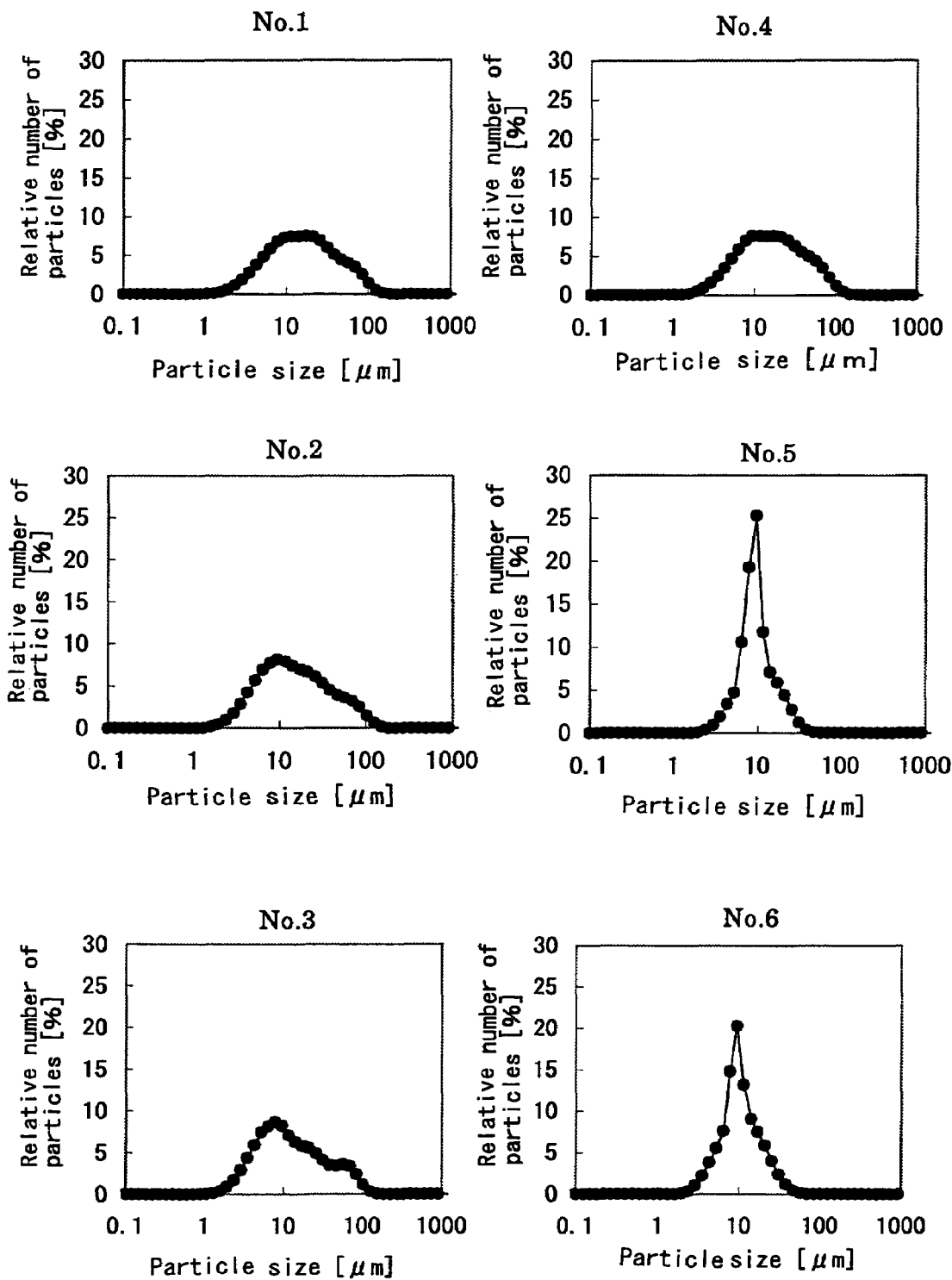
FIG. 2 shows a particle size distribution profile of the particles of the lyophilized formulation of each lot in Experimental Example 1.

To the aforementioned lyophilized formulation for injection (20 mg) was added 4 mL of isopropyl myristate to give a suspension. Using an upright differential interference microscope manufactured by Olympus Corporation, the particle shape was observed, and the particle distribution was measured using a laser diffraction type particle size distribution analyzer SALD-3000 manufactured by Shimadzu Corporation. The results are shown in FIG. 1 and FIG. 2.

The particle distribution measurement conditions for laser diffraction type particle size distribution analyzer SALD-3000 manufactured by Shimadzu Corporation are as follows.

Suspending/diluting solvent: IPM-EX (isopropyl myristate)
Concentration of active component at the time of measurement: about 0.03 mg/mL
Refractive index: 2.40-0.20i
Basis of distribution: volume
Sieving: minus sieve
Distribution function: non-conversion
Smoothing level: 0
Data shift: 0
Number of measurement: once
Measured absorbance range: maximum value 0.200, minimum value 0.010

As a result, observation of the particle shape mainly revealed two types. One is a lot wherein most of the particles are amorphous and large amorphous particles exceeding 50-100 μm are contained, and the other is a lot mostly consisting of spherical particles of 5-20 μm. The particle distribution of these lots was classified into two types: one having a D90% value of 50-100 μm and the other having a D90% value of 10-30 μm, as shown in Table 1. The particle size distribution profile is shown in FIG. 2. Therein, the lots having a D90% value of 10-30 μm (Formulation Nos. 5 and 6) correspond to Examples of the present invention and other lots (Formulation Nos. 1-4) correspond to Comparative Examples (Table 1).

TABLE 1

| Formulation No. | Particle distribution of particles of lyophilized formulation | | |
|---|---|---|---|
| | Particle distribution [μm] | | |
| | D90% | D75% | D50% |
| 1 | 52.1 | 28.3 | 14.1 |
| 2 | 51.1 | 26.2 | 12.6 |
| 3 | 48.7 | 22.7 | 10.1 |
| 4 | 50.3 | 28.6 | 14.4 |
| 5 | 16.0 | 11.3 | 8.5 |
| 6 | 19.8 | 13.1 | 9.1 |

Experimental Example 1-2

To the lyophilized formulation for injection (20 mg) obtained in Experimental Example 1 was added 1 mL of an iodine addition product of the ethyl ester of the fatty acids of poppyseed oil (water content 0.4-0.7 mg/mL) to give a suspension of cis[((1R,2R)-1,2-cyclohexanediamine-N,N') bis(tetradecanoyloxy)]platinum(II). The concentration of the active ingredient in the suspension was 20 mg/mL. Then, the suspension was stood still at room temperature, and changes in the viscosity with the lapse of time were measured.

A simple viscometer to be used for the viscosity measurement was calibrated. A standard solution for viscosity calibration (Japanese Industrial Standard JIS Z8809) JS50, JS200 was sucked from a flow opening of the simple viscometer and the time necessary for flowing a predetermined distance was measured twice with a stopwatch and recorded down to the second decimal place (unit second). Based on the average value (down to the second decimal place (unit second)) of the obtained two flow times, the K value of each standard solution was determined down to the fourth decimal place from the formula (1). In addition, the K values of the respective standard solutions were averaged and determined down to the fourth decimal place and taken as the K value of the simple viscometer to be used. The standard solution for viscosity calibration was maintained at a liquid temperature of 20° C. in a constant temperature chamber and the like and used for the measurement immediately after taking out.

$$K \text{ value} = \text{kinematic viscosity [mm}^2\text{/s] at } 20° \text{C.} \div \text{average value [sec] of flow time} \quad \text{formula (1)}$$

Then, the viscosity of a suspension of cis[((1R,2R)-1,2-cyclohexanediamine-N,N')bis(tetradecanoyloxy)]platinum(II) in an iodine addition product of the ethyl ester of the fatty acids of poppyseed oil was measured per vial with the lapse of time at room temperature. That is, a suspension of an iodine addition product of the ethyl ester of the fatty acids of poppyseed oil was sucked from a flow opening of the calibrated simple viscometer and the time necessary for flowing a predetermined distance was measured twice with a stopwatch and recorded down to the second decimal place (unit second). Based on the average value (down to the first decimal place (unit second)) of the obtained two flow times, the viscosity was calculated and determined down to the first decimal place from the formula (2).

$$\text{viscosity [mPa·s]} = \text{average value [sec] of flow time} \times K \text{ value} \times \text{density of iodine addition product of the ethyl ester of the fatty acids of poppyseed oil } 1.281 \text{ [g/cm}^2\text{]} \quad \text{formula (2)}$$

Figure 3:
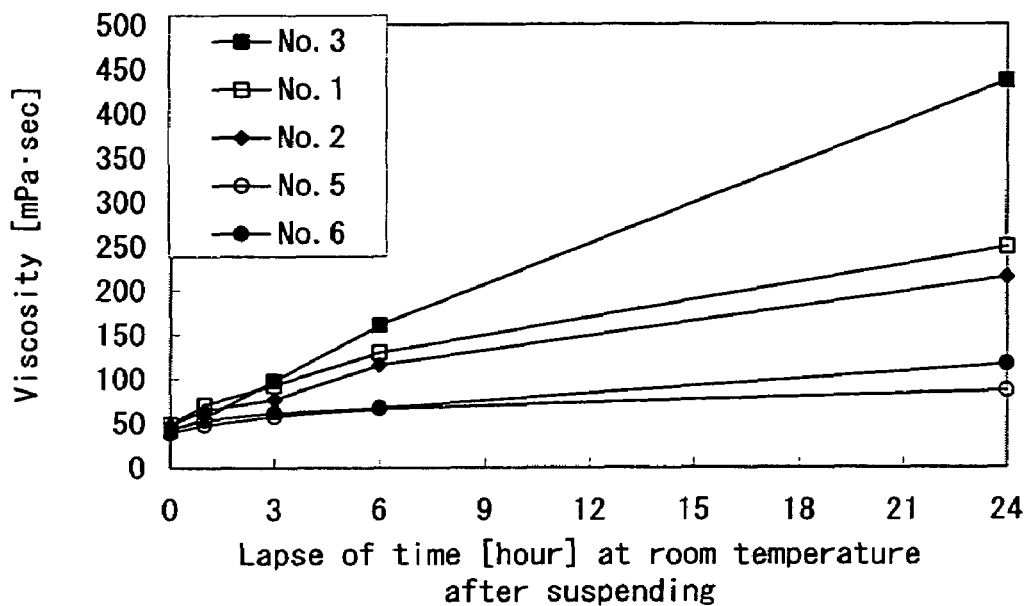
FIG. 3 includes drawings showing changes with time in the viscosity of the lyophilized formulations after suspending in an iodine addition product of the ethyl ester of the fatty acids of poppyseed oil in Experimental Example 1.
Figure 3:
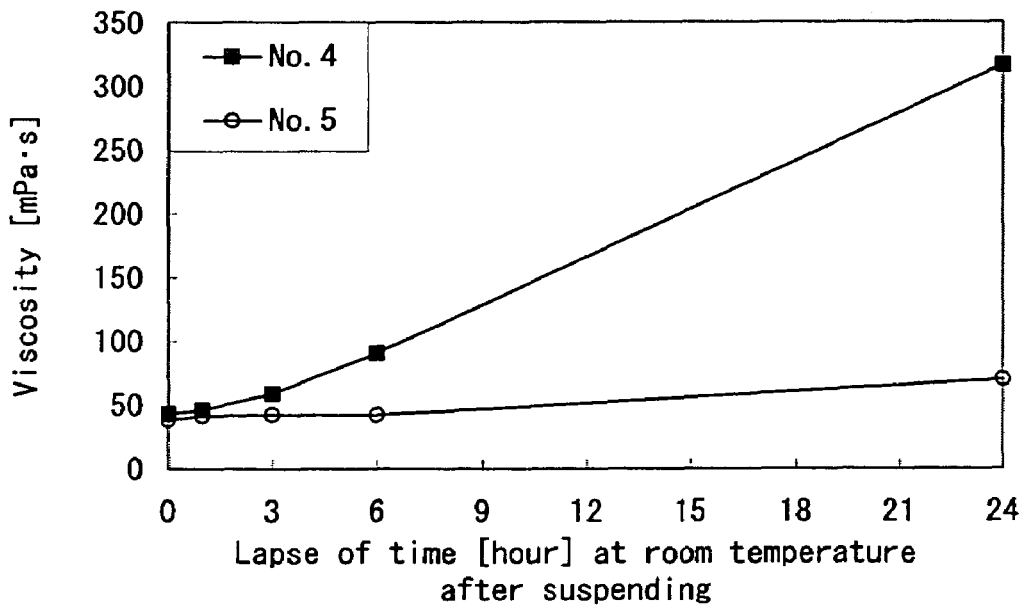

The results of viscosity measurement are shown in FIG. 3.

From the results of Experimental Example 1-1 and Experimental Example 1-2, it is suggested that the particle distribution or particle shape is involved in the difference in the viscosity increase.

Experimental Example 2

Then, how the properties of the formulation after lyophilizing change was examined when the water content of a drug solution before freezing is changed. cis[((1R,2R)-1,2-Cyclohexanediamine-N,N')bis(tetradecanoyloxy)]platinum(II) monohydrate was dissolved in 2-methyl-2-propanol and water content was measured using a Karl-Fischer moisture meter. A calculated amount of distilled water for injection to make the water content 0.5 mg/mL-6.0 mg/mL was added to give drug solutions having different water contents. The lots having a water content of 1-4 mg/mL correspond to Examples of the present invention and the lots other than those correspond to Comparative Examples. Each drug solution was sterilized by filtration through a filter (pore size: 0.22 μm). Each of the drug solutions was filled in a vial by 5 mL and halfway stoppered. The vial was placed on a shelf set at 30° C. and gradually cooled to −40° C. over about 2 hr to allow for freezing. It was lyophilized to give a lyophilized formulation for injection.

Experimental Example 2-1

Figure 4:
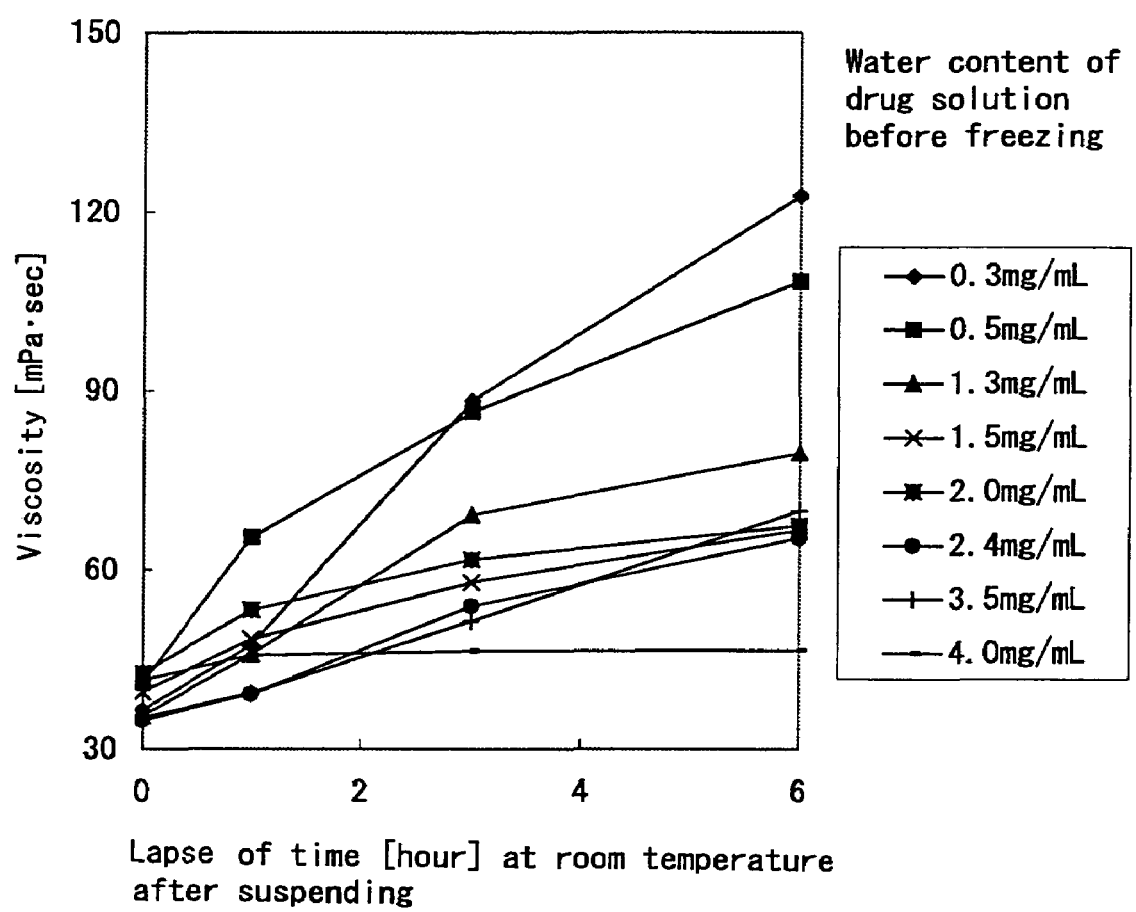
FIG. 4 is a drawing showing water content of drug solutions before freezing and changes with time in the viscosity of the lyophilized formulations after suspending in an iodine addition product of the ethyl ester of the fatty acids of poppyseed oil in Experimental Example 2.

The lyophilized formulation for injection (20 mg) obtained in Example 2 was evaluated for the changes in the viscosity after suspending in an iodine addition product of the ethyl ester of the fatty acids of poppyseed oil, by the same method as in Experimental Example 1-2. The results are shown in FIG. 4. It was found that increased water contents before freezing were associated with the prevention of increase in the viscosity with the lapse of time.

Experimental Example 2-2

The particle size distribution of the lyophilized formulation for injection (20 mg) obtained in Experimental Example 2 was measured by the same method as in Experimental Example 1-1. The results are shown in FIG. 5, FIG. 6 and Table 2.

TABLE 2

Figure 5:
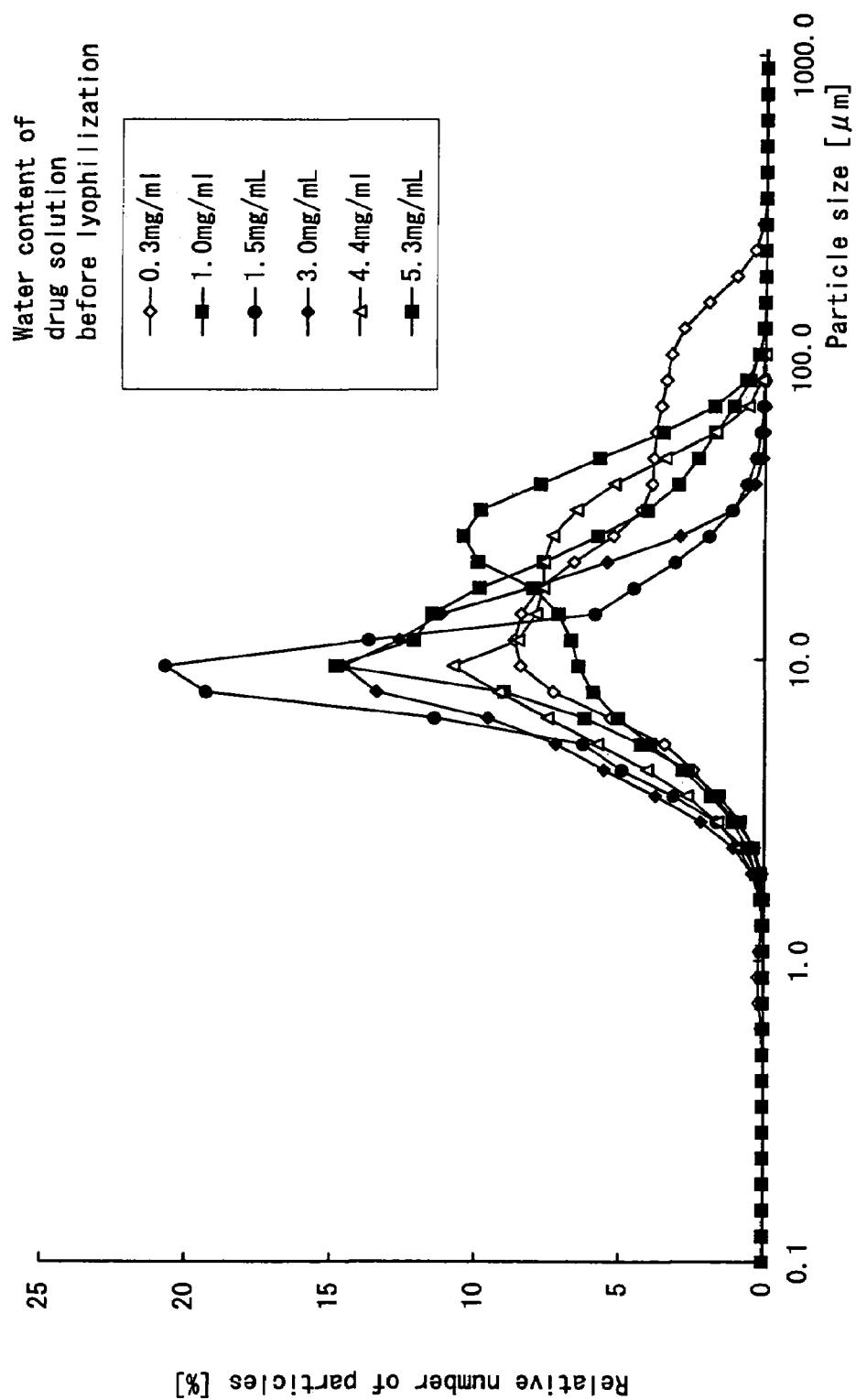
FIG. 5 is a particle size distribution profile after lyophilization due to different water contents of drug solutions in Experimental Example 2.
Figure 6:
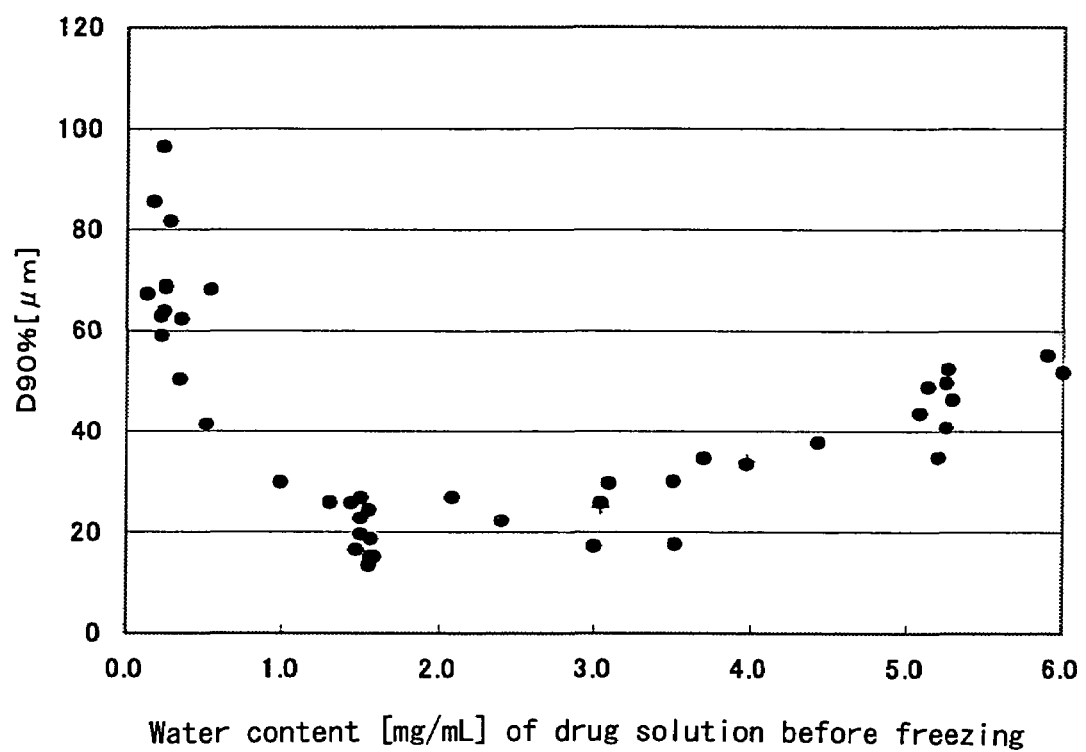
FIG. 6 is a drawing showing the relationship between water contents of drug solutions before freezing and D90% values of the particles of the lyophilized formulations in Experimental Example 2.
Figure 7A:
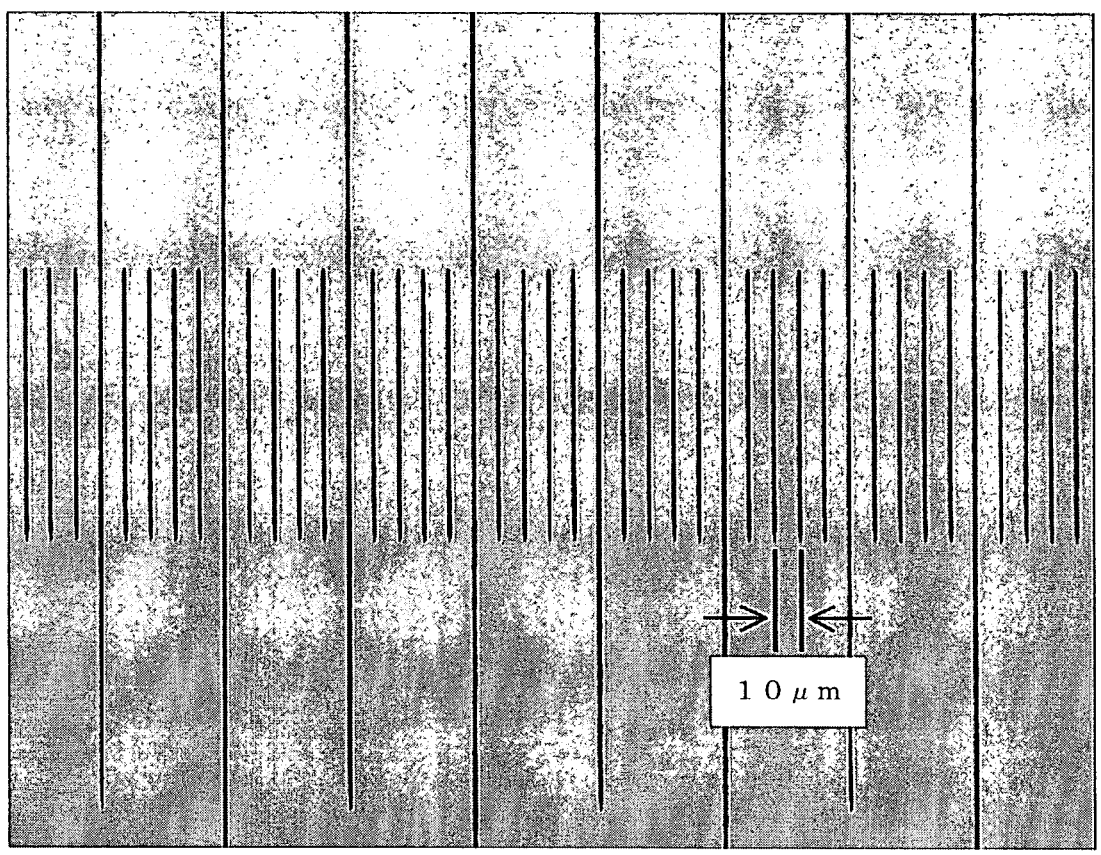
FIGS. 7B-D are outputs of differential interference microscopic observation of the particles of the lyophilized formulations in Experimental Example 2 and FIG. 7A is an output of microscopic observation at the scale of the magnification in FIGS. 7B-D (minimum scale being 10 μm).
Figure 7B:
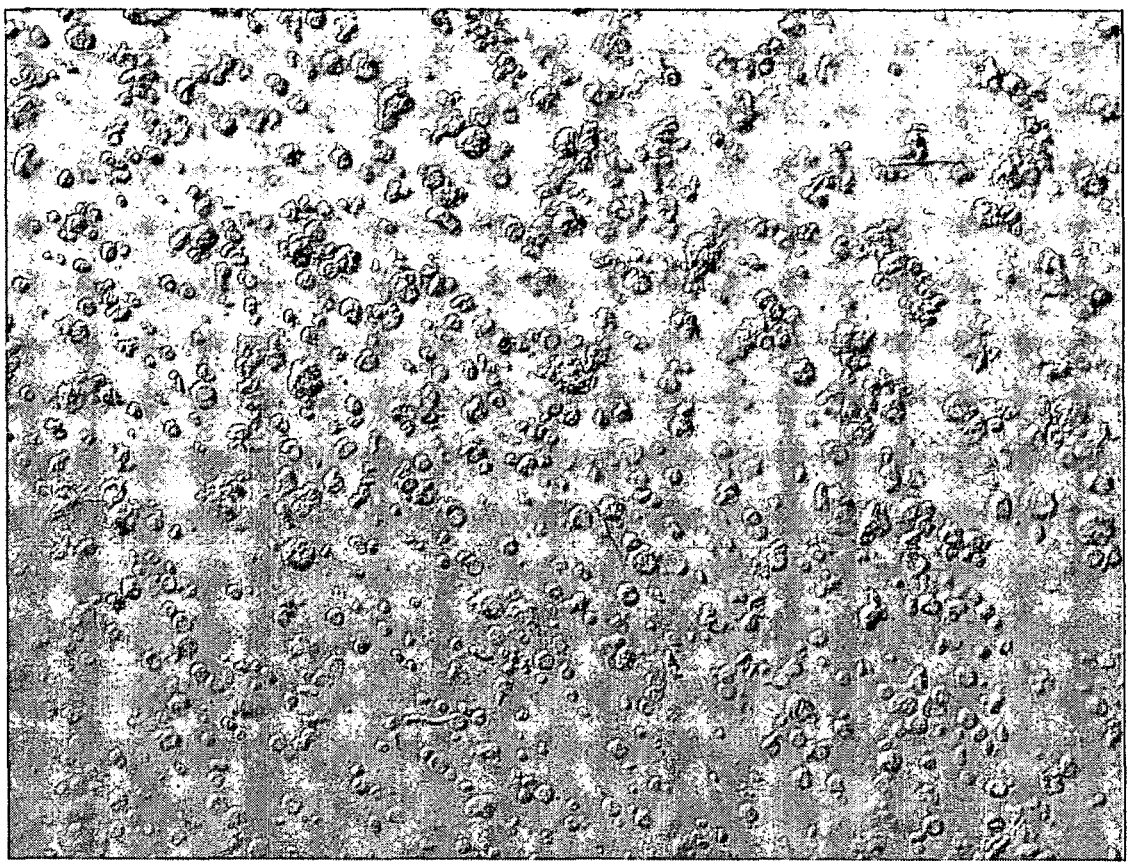
Figure 7C:
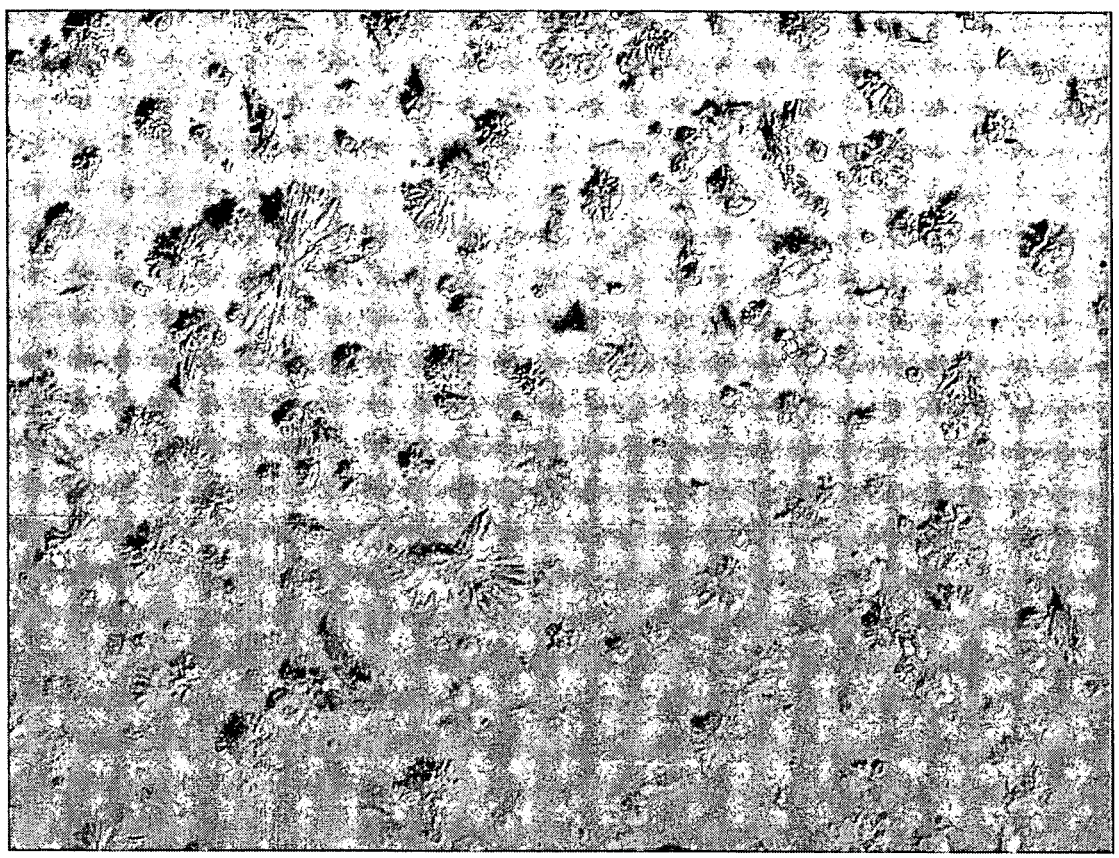
Figure 7D:

Particle distribution data of graph data of FIG. 5

| Water content of drug solution before lyophilization | Particle distribution [µm] | | |
|---|---|---|---|
| | D50% | D75% | D90% |
| 0.3 mg/mL | 17.0 | 43.3 | 97.3 |
| 1.0 mg/mL | 11.2 | 18.0 | 30.0 |
| 1.5 mg/mL | 7.9 | 10.1 | 13.6 |
| 3.0 mg/mL | 8.4 | 12.6 | 17.5 |
| 4.4 mg/mL | 11.2 | 21.1 | 32.7 |
| 5.3 mg/mL | 17.3 | 28.1 | 40.5 |

When the water content before lyophilization was less than 0.5 mg/mL, the particle size distribution was broad. As the water content increased, the relative number of particles in greater particle size fractions decreased and at a water content of about 1.5 mg/mL, sharp distribution was found with a comparatively narrow distribution width. As the water content increased, large particle size fractions increased and became broad, wherein broad distribution was found with the peak top (highest frequency particle size fraction) shifted to a greater particle size side from the water content of about 4.0 mg/mL. When the changes in the particle distribution were compared in terms of D90% values, the water content before lyophilization of less than about 0.5 mg/mL showed a value of not less than 50 µm, which gradually diminished as the water content increased, showing a value of about 20 µm near the water content of about 1.5 mg/mL. Further, when the water content increased, the D90% value became greater again, and at about 4.0-about 5.0 mg/mL, it showed a value of about 35-about 50 µm.

Experimental Example 2-3

To the lyophilized formulation for injection (20 mg) obtained in Experimental Example 2 was added 4 mL of isopropyl myristate to give a suspension, and the shape of the particles in the suspension was observed using a differential interference microscope manufactured by Olympus Corporation by the same method as in Experimental Example 1-1. The results are shown in FIG. 7. When the water content before lyophilization was less than about 0.5 mg/mL, most particles were amorphous, containing amorphous particles exceeding about 50-about 100 µm. The particle surface had no regularity of unevenness. When the water content before lyophilization increased and reached about 1.5-about 3.0 mg/mL, most particles were spherical particles of about 5-about 30 µm, and amorphous particles were hardly acknowledged. As the water content increased, individual particles became larger and the surface of the spherical particles began to grow like needles. Further, when the water content became about 5.0 mg/mL, the surface of the spherical particles of about 30-about 50 µm became needles (Table 3).

TABLE 3

Particle shape of particles of lyophilized formulations having various water contents of drug solutions before freezing

| Water content before lyophilization (mg/mL) | Particle shape |
|---|---|
| less than 0.5 | Mixture of amorphous particles of about 50-about 100 µm |
| 1.0 | Spherical particles of about 5-about 20 µm. A small amount of amorphous particles of about 50 was present. |
| 1.5 | Spherical particles of about 5-about 20 µm |
| 3.0 | Spherical particles of about 10-about 30 µm. Particle surface slightly became needles. |
| 5.3 | Surface of spherical particles of about 30-3 about 50 µm became needle-like. |

Experimental Example 2-4

The lyophilized formulation for injection (20 mg) obtained in Experimental Example 2 was measured for the time it can stay stably as a uniform suspension without separating into two layers after suspending. To the lyophilized formulation for injection (20 mg) was added 1 mL of an iodine addition product of the ethyl ester of the fatty acids of poppyseed oil (water content 0.4-0.6 mg/mL) to give a suspension. The dissolution state of the suspension was observed with the lapse of time. As a result, as the water content before freezing increased, the active component tended to precipitate in the lower layer of the suspension, and the time before separation into two layers tended to become short (Table 4).

TABLE 4

Stability of lyophilized formulations with different water contents of drug solutions before freezing, after suspending in iodine addition product of the ethyl ester of the fatty acids of poppyseed oil

| Water content [mg/mL] of drug solution before lyophilization | Uniformity of suspension and lapse of time after suspending | | | |
|---|---|---|---|---|
| | 1 hr | 3 hr | 6 hr | 24 hr |
| <0.5 | uniform | uniform | uniform | uniform |
| 1.0 | uniform | uniform | uniform | uniform |

TABLE 4-continued

Stability of lyophilized formulations with different water contents of drug solutions before freezing, after suspending in iodine addition product of the ethyl ester of the fatty acids of poppyseed oil

| Water content [mg/mL] of drug solution before lyophilization | Uniformity of suspension and lapse of time after suspending | | | |
|---|---|---|---|---|
| | 1 hr | 3 hr | 6 hr | 24 hr |
| 1.5 | uniform | uniform | uniform | uniform |
| 2.0 | uniform | uniform | uniform | uniform |
| 3.0 | uniform | uniform | uniform | uniform |
| 4.0 | uniform | uniform | uniform | two layer separation |
| 5.1 | uniform | uniform | two layer separation | two layer separation |
| 6.2 | uniform | uniform | two layer separation | two layer separation |

Experimental Example 2-5

The lyophilized formulation for injection (20 mg) obtained in Experimental Example 2 was compared for the operability of suspending in an iodine addition product of the ethyl ester of the fatty acids of poppyseed oil. To the lyophilized formulation for injection (20 mg) obtained in Experimental Example 2 was added 1 mL of an iodine addition product of the ethyl ester of the fatty acids of poppyseed oil (water content 0.4-0.6 mg/mL) and which of the following operations can give a uniform suspension was evaluated. An iodine addition product of the ethyl ester of the fatty acids of poppyseed oil was added, and after allowing it to blend with the active component while turning the vial, one uniformly suspended only by lightly shaking the vial with a hand was evaluated to be "easy", and one that failed to become sufficiently uniform by the above operation and could be suspended only by shaking the vial while hitting the bottom thereof with a hand was evaluated to be "difficult". As a result, as the water content before freezing increased, the suspendability tended to become difficult (Table 5).

TABLE 5

Suspendability of lyophilized formulations having different water contents of drug solutions before freezing, in an iodine addition product of the ethyl ester of the fatty acids of poppyseed oil

| Water content of drug solution before freezing [mg/mL] | Suspendability |
|---|---|
| 0.5 | easy |
| 1.5 | easy |
| 3.5 | easy |
| 5.0 | easy |
| 6.0 | difficult |

From the above results, due to the changes in the water content of the drug solution before freezing, the properties of the formulation after lyophilization markedly changed, and it was clarified that a formulation easy to handle can be obtained by controlling the water content. That is, when the lyophilized formulation for injection (20 mg) is to be placed on a lyophilizer shelf (temperature 30° C.) and allowed to freeze by gradually cooling to −40° C. over about 2 hr, and lyophilized, the water content is preferably not less than about 1.5 mg/mL in consideration of prevention of increase in viscosity, and the water content is preferably not more than about 4.0 mg/mL in consideration of uniformity after suspending (free of separation into two layers for a long time after suspending) and easiness of suspending operation, which in turn suggests the optimal range to be 1.5-4.0 mg/mL. In addition, it was suggested that a stable lyophilized formulation for injection, which is easy to handle, can be obtained by controlling the particle distribution of the active ingredient powder after lyophilization to not more than about 33 μm in a D90% value, or as spherical particles (Table 6).

TABLE 6

List of comparison of formulation properties of lyophilized formulations having different water contents of drug solutions before freezing

| Water content [mg/mL] of drug solution before freezing | Particle distribution (D90%) [μm] | Particle shape | Viscosity stability | Time capable of maintaining uniform state without separating into two layers after suspending | Suspendability |
|---|---|---|---|---|---|
| <0.5 | about 40-about 100 | amorphous | x | 24 hr< | easy |
| 1.0 | about 20-about 30 | mostly spherical particles | ○ | | |
| 1.5 | about 10-about 25 | | | | |
| 2.0 | about 20-about 25 | | | | |
| 3.0 | about 20-about 30 | | | | |
| 4.0 | about 30-about 35 | | | 6 hr | |
| 5.0 | about 37-about 50 | particles with needle spherical particle surface | ⊙ | 3 hr | |
| 6.0 | about 50-about 60 | | | 3 hr | difficult |

The viscosity stability is based on the following evaluation criteria.
⊚; viscosity at 24 hrs after suspending is less than two times the viscosity immediately after suspending
○; viscosity at 3 hrs after suspending is less than two times the viscosity immediately after suspending
x; viscosity at 3 hrs after suspending is not less than two times the viscosity immediately after suspending Experimental Example 3

The water content of the drug solutions before lyophilization was changed in the range of about 1.5-about 6 mg/mL, the solutions were filtered for sterilization, filled in vials, and lyophilized under various freezing conditions to give 20 mg formulations and 80 mg formulations. The obtained formulations were evaluated for particle distribution (D90% value), particle shape, changes in viscosity after suspending in an iodine addition product of the ethyl ester of the fatty acids of poppyseed oil, stability after suspending (time capable of staying a uniform suspension without separating into two layers) and suspendability.

Experimental Example 3-1

Figure 8:
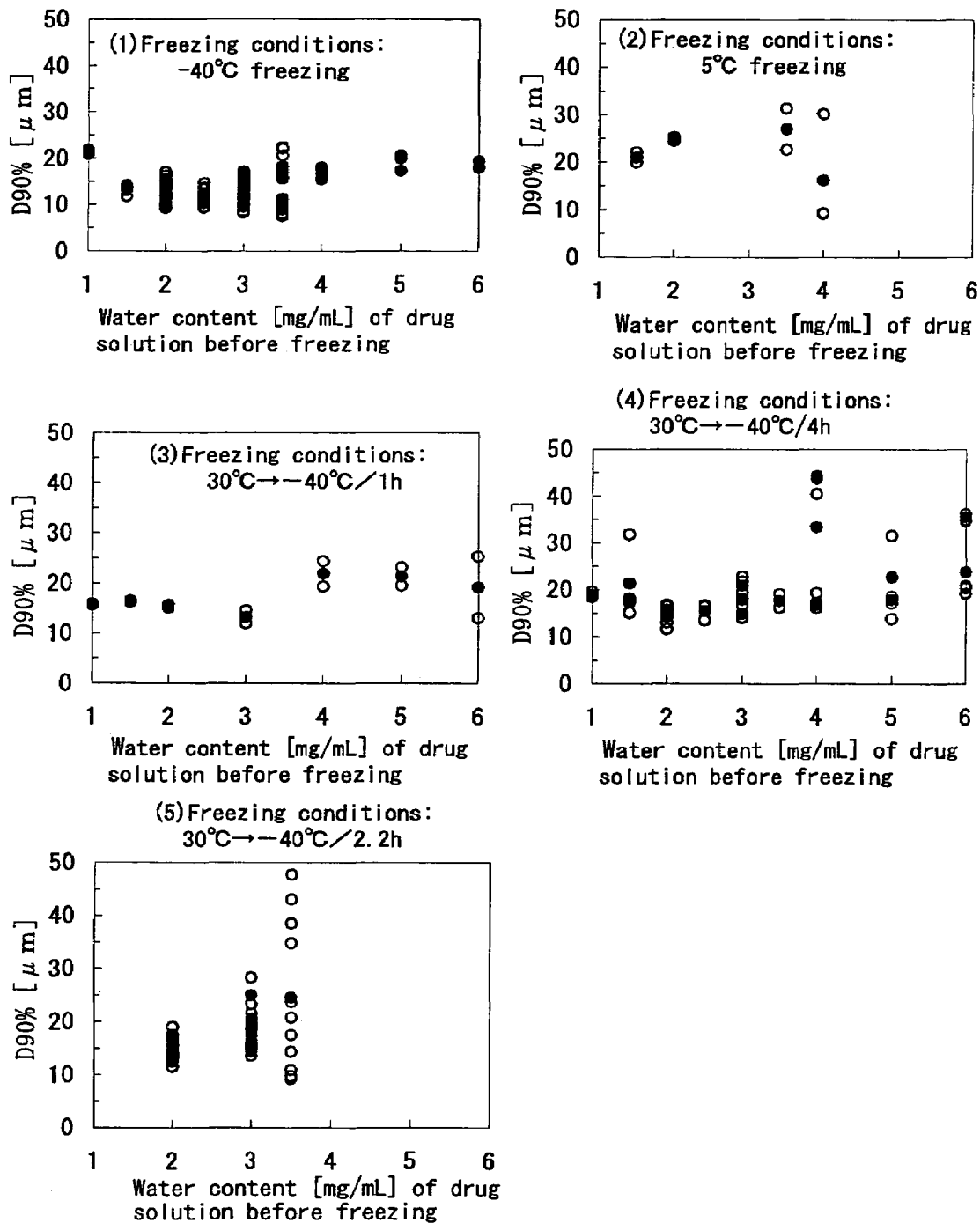
FIG. 8 includes drawings showing the relationship between water contents of the drug solutions of 20 mg formulations and the freezing conditions, and D90% values.
Figure 9:
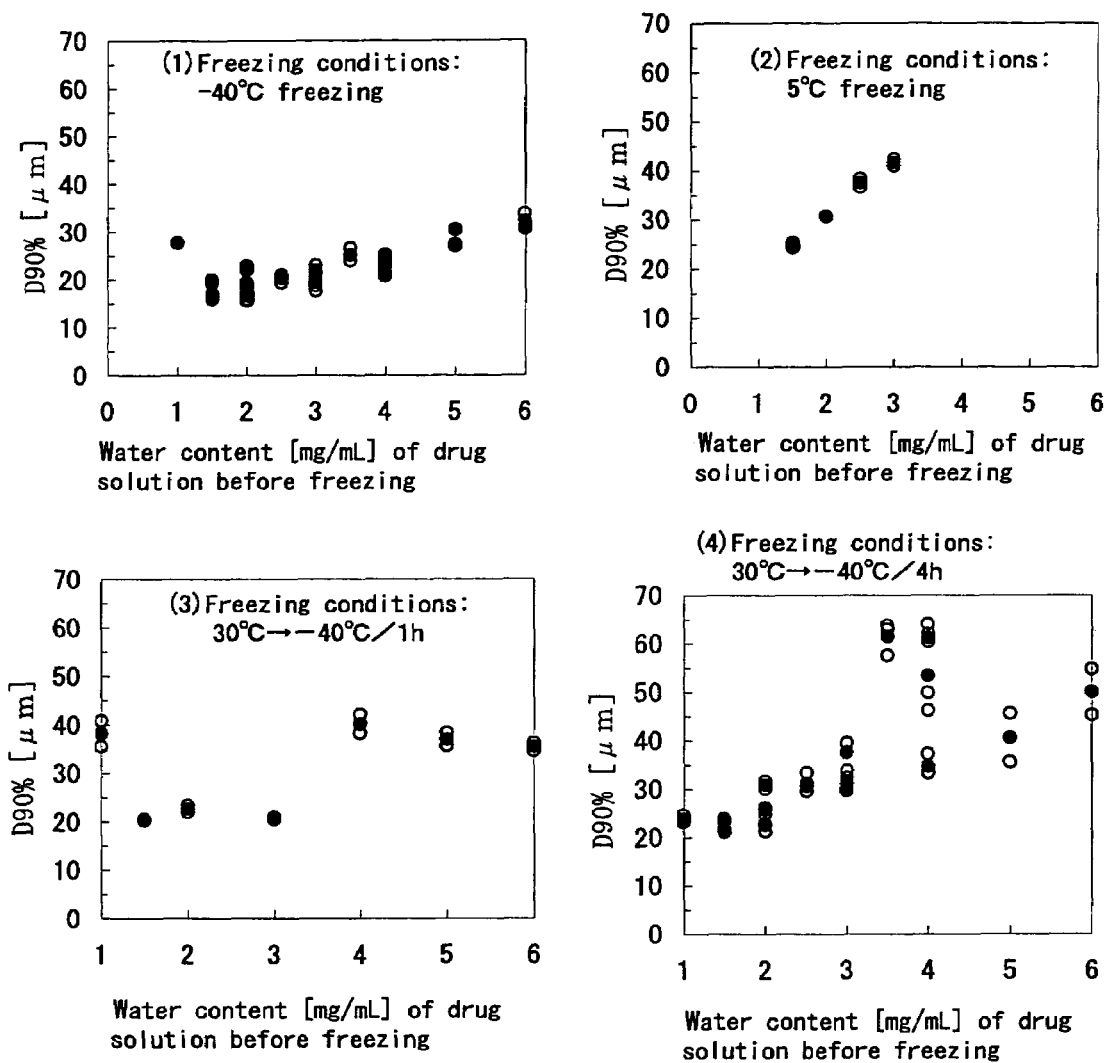
FIG. 9 includes drawings showing the relationship between water contents of the drug solutions of 80 mg formulations and the freezing conditions, and D90% values.
Figure 10A:
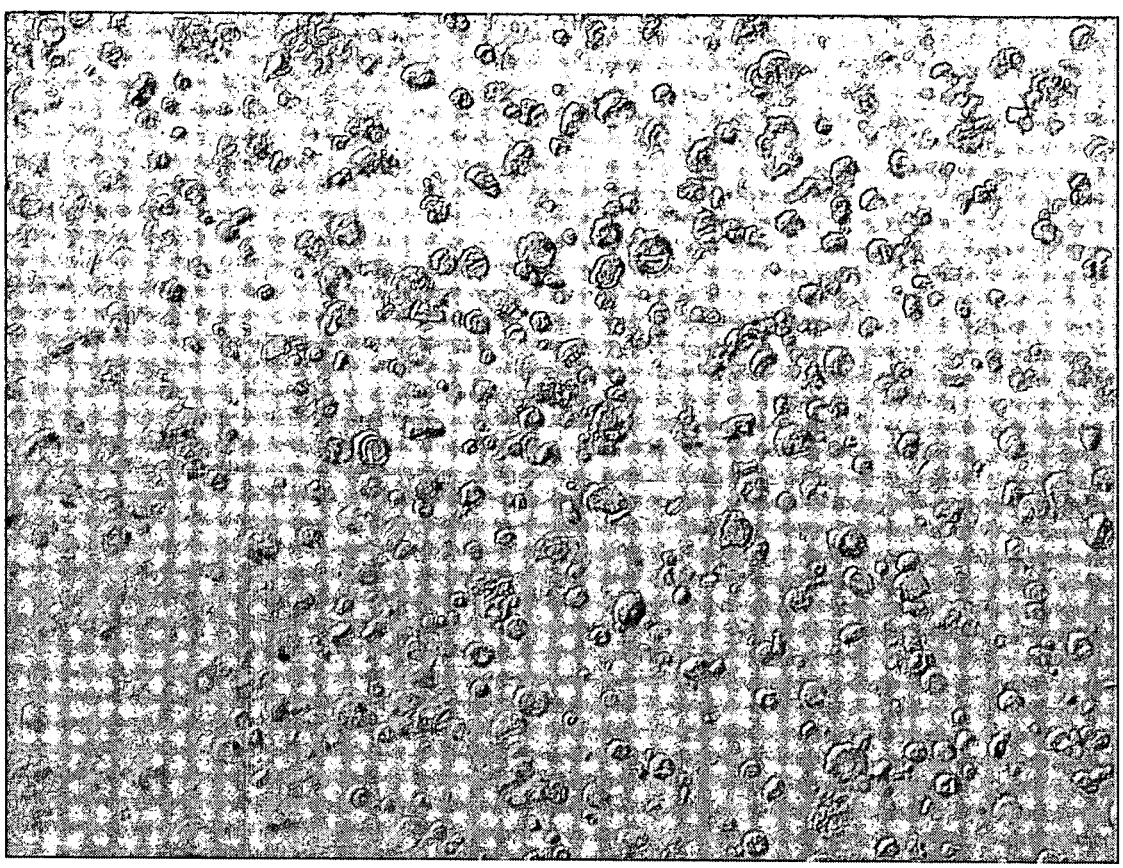
Figure 10B:
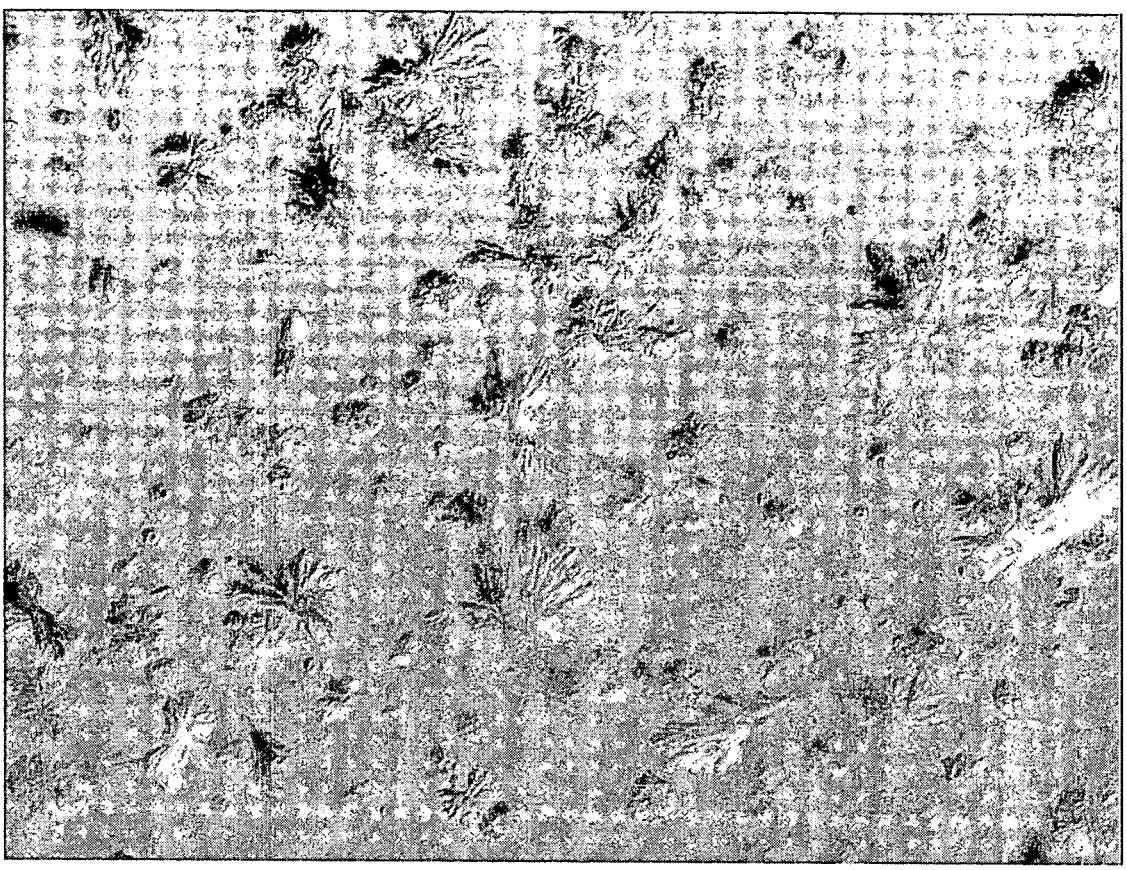
Figure 10C:
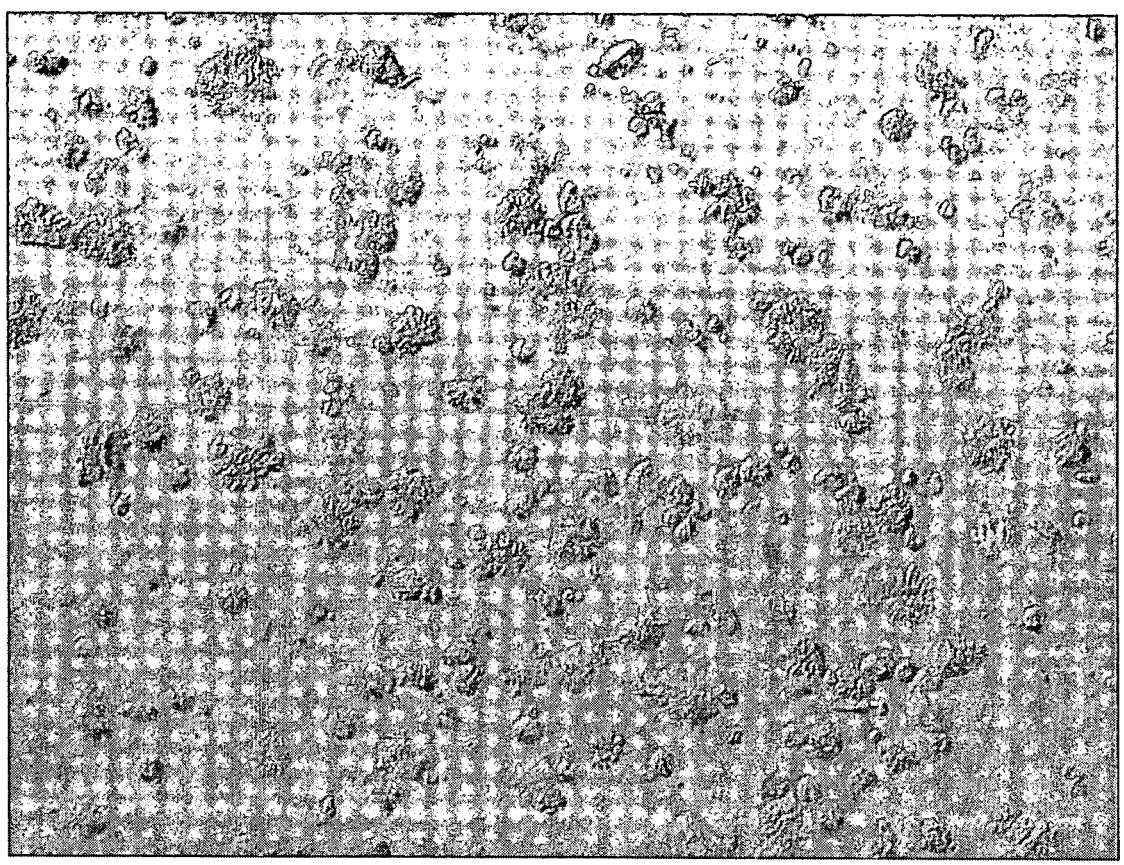
Figure 10D:
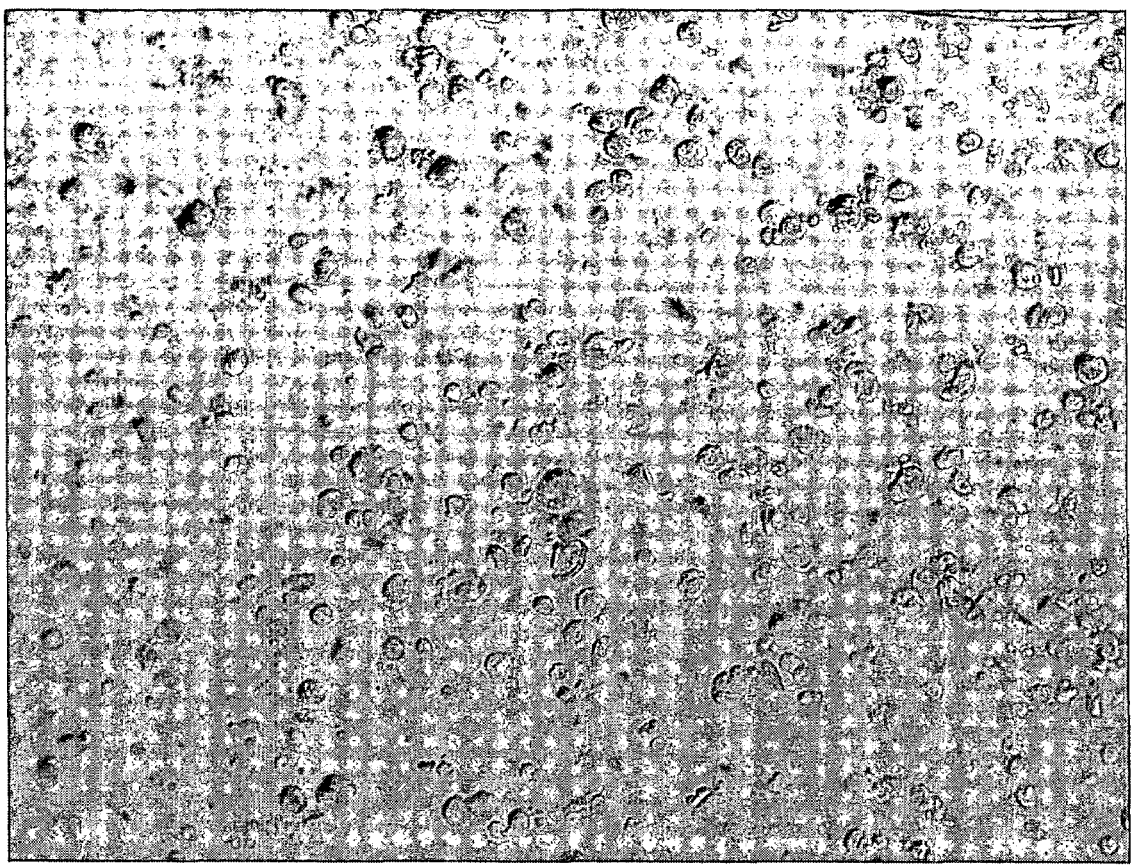
Figure 10E:
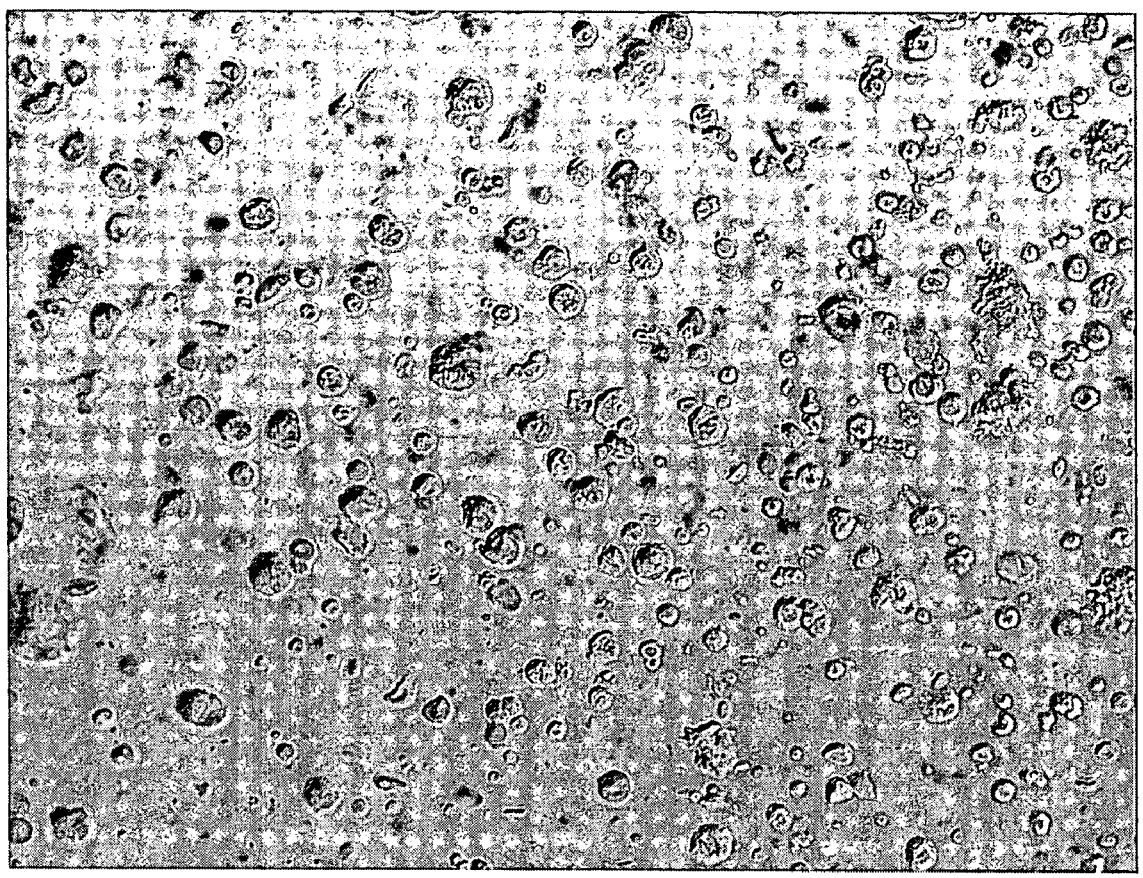
Figure 10F:
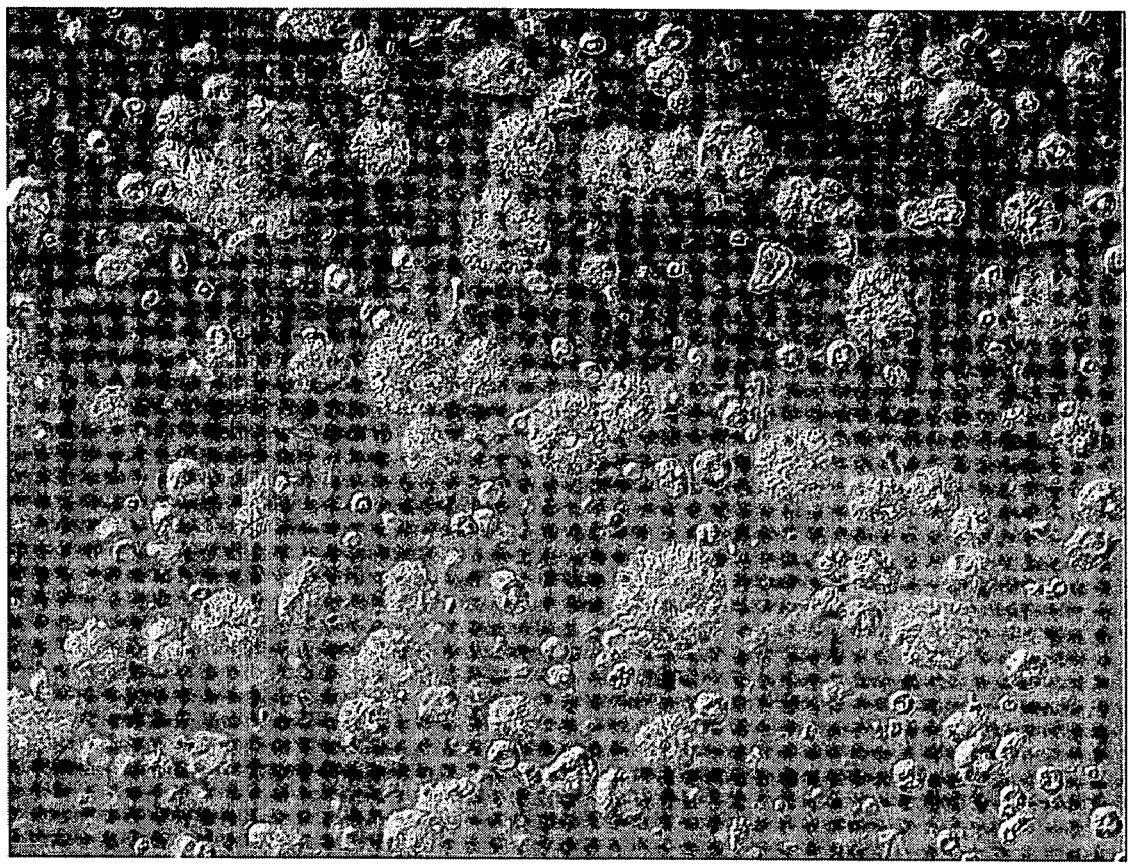

The 20 mg formulations and 80 mg formulations obtained in Experimental Example 3 were evaluated for the particle distribution (D90% value) and particle shape. The particle distribution was measured by suspending the formulation in isopropyl myristate and using a laser diffraction type particle size distribution analyzer (SALD-3000, manufactured by Shimadzu Corporation) in the same manner as in the method of Experimental Example 1. The results are shown in FIG. 8 and FIG. 9. For the particle shape, the formulation was suspended in isopropyl myristate and the shape of the particles in the suspension was observed under an upright differential interference microscope manufactured by Olympus Corporation in the same manner as in the method of Experimental Example 1. The results are shown in FIG. 10.

As a result, the particle distribution (D90% value) and particle shape of both the 20 mg formulations and 80 mg formulations changed under any freezing conditions, depending on the water content of drug solution before lyophilization as acknowledged in Experimental Example 2. In the 20 mg formulations, the D90% value became not more than 33 μm by setting the water content of drug solution before lyophilization to the range of about 2.0-about 3.0 mg/mL under any freezing conditions, and in the particle shape observation, the spherical particles of about 10-about 20 μm were confirmed. Under the conditions including freezing at −40° C., and charging at 30° C. and cooling to −40° C. in 1 hr (hereinafter to be represented as "30° C.→−40° C./1 h condition"), the D90% value became not more than 33 μm even when the water content of drug solution before lyophilization was the highest, and spherical particles of about 10-about 20 μm were acknowledged by particle shape observation. Under other freezing conditions, the D90% values dispersed greatly between lots and vials when the water content was not less than about 3.0 mg/mL.

In the 80 mg formulations, the D90% value became not more than 33 μm in the water content range of drug solution before lyophilization of about 1.5-about 3.0 mg/mL under the conditions of freezing at −40° C. and 30° C.→−40° C./1 h freezing, where particularly by freezing at −40° C., the D90% value became not more than 33 μm in the water content range of drug solution before lyophilization of about 1.5-about 5.0 mg/mL, and spherical particles of about 10-about 20 μm were acknowledged by particle shape observation. Under other freezing conditions, the water content range of drug solution to obtain a lyophilized formulation having a D90% value of not more than 33 μm became as narrow as about 0.5 mg/mL, and the D90% value became larger than by freezing at −40° C. From these, −40° C. freezing conditions were most superior from the viewpoints of control of the D90% value and control of the particle shape (Table 7).

TABLE 7

Particle shape after lyophilization that is formed by different freezing conditions and different water content of drug solution before freezing

| W.C. [mg/mL] | Freezing conditions | | | | | | | | | |
|---|---|---|---|---|---|---|---|---|---|---|
| | −40° C. | | 5° C. | | 30° C. →−40° C./1 h | | 30° C. →−40° C./4 h | | 30° C. →−40° C./2.2 h | |
| | 20 mg | 80 mg | 20 mg | 80 mg | 20 mg | 80 mg | 20 mg | 80 mg | 20 mg | 80 mg |
| 1.0 | Δ | Δ | — | — | Δ | Δ | Δ | Δ | — | — |
| 1.5 | ○ | ○ | ○ | ○ | ○ | ○ | ○ | ○ | — | — |
| 2.0 | ○ | ○ | ● | ● | ○ | ○ | ○ | ○ | ○ | — |
| 2.5 | ○ | ○ | — | ●-♦ | — | — | ○ | ●-♦ | — | — |
| 3.0 | ○ | ○ | — | ♦ | ○ | ○ | ○ | ♦ | ● | — |
| 3.6 | ○ | ● | ♦ | — | — | — | ○ | ♦ | ♦ | — |
| 4.0 | ○ | ●-♦ | ♦ | — | ♦ | ♦ | ♦ | ♦ | — | — |
| 5.0 | ● | ●-♦ | — | — | ♦ | ♦ | ♦ | ♦ | — | — |
| 6.0 | ● | ●-♦ | — | — | ♦ | ♦ | ♦ | ♦ | — | — |

Note:
The symbols in the Table mean the following particle shapes.
—: not conducted
Δ: amorphous particles
○: spherical particles
●: particle surface of spherical particles slightly became needles,
♦: particle surface of spherical particles became needle-like Experimental Example 3-2

Figure 11:
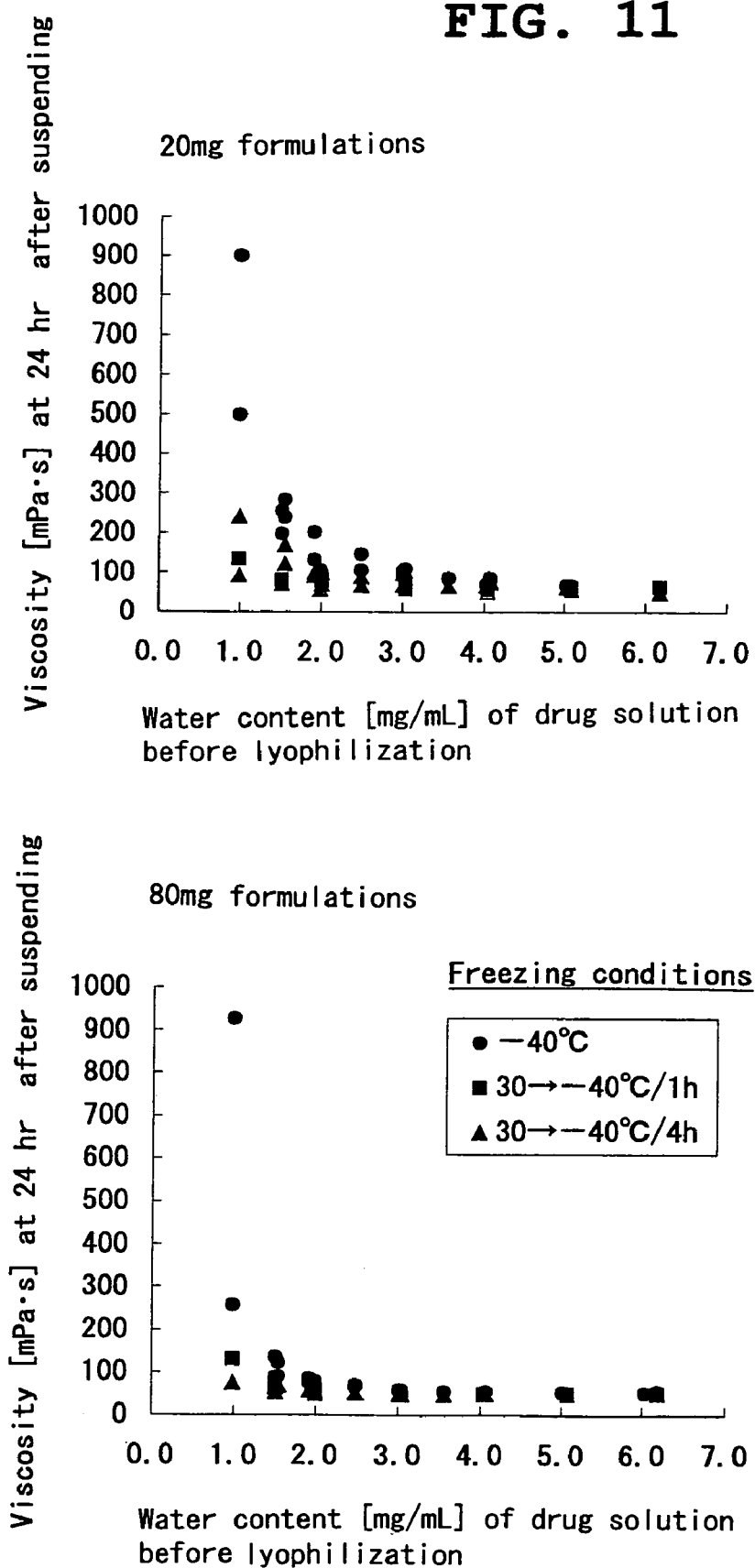
FIG. 11 includes drawings showing the freezing conditions, water contents of the drug solutions before freezing and viscosity at 24 hrs after suspending the lyophilized formulations in an iodine addition product of the ethyl ester of the fatty acids of poppyseed oil, in Experimental Example 3.

The 20 mg formulations and 80 mg formulations obtained in Experimental Example 3 were evaluated for changes in viscosity after standing at room temperature for 24 hr following suspending in an iodine addition product of the ethyl ester of the fatty acids of poppyseed oil and. An iodine addition product of the ethyl ester of the fatty acids of poppyseed oil (water content 0.4-0.7 mg/mL) was added to each formulation such that the concentration of the active component was about 20 mg/mL and uniformly suspended therein. The viscosity after standing at room temperature for 24 hr was measured with a simple flow viscometer according to the method described in Experimental Example 1-2. The results are shown in FIG. 11. Under all freezing conditions, the higher the water content of the drug solution before lyophilization was, the lower the viscosity became. With the same water content, −40° C. freezing tended to show higher viscosity as compared to other freezing conditions and the 20 mg formulations tended to show higher viscosity than did the 80 mg formulations.

Figure 12:
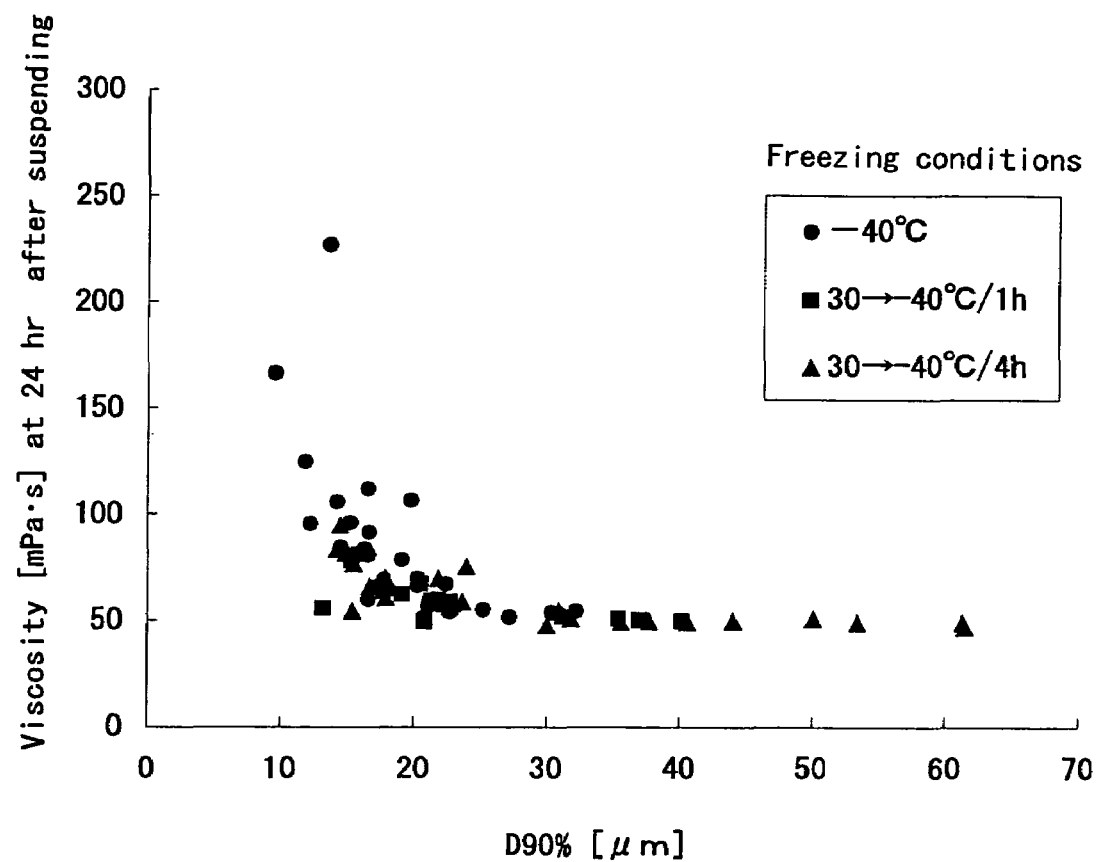
FIG. 12 shows the relationship between D90% value and viscosity at 24 hrs after suspending the lyophilized formulations in an iodine addition product of the ethyl ester of the fatty acids of poppyseed oil, in Experimental Example 3.

Moreover, the D90% value and viscosity at 24 hr after suspending are shown in FIG. 12. It was found that, irrespective of freezing conditions and formulation dose, a formulation nearly free of amorphous particles at a drug solution water content before freezing of not less than 1.5 mg/mL showed lower viscosity at 24 hr after suspending as the D90% value increased, and the viscosity did not increase easily.

iodine addition product of the ethyl ester of the fatty acids of poppyseed oil, without separating into two layers, by the same method as in Experimental Example 2. As a result, when the lapse of time after suspending became longer, the active component tended to precipitate in the lower layer of the suspension, resulting in two layer separation, as the water content before freezing increased under any conditions. This tendency was acknowledged more in the 80 mg formulations from lower water contents than in the 20 mg formulations. However, under −40° C. freezing conditions, even when the water content was high, the formulations could exist stably as uniform suspensions not easily separated into two layers, as compared to the conditions comprising gradually cooling from 30° C. to −40° C. to allow for freezing.

The relationship among the stability after suspending, D90% value and particle shape was examined, and it was found that, irrespective of the dose of the formulation and freezing conditions, the formulations easily separated into two layers when the D90% value increased to not less than 40 μm and as the particle shape grew needle-like from the surface of spherical particles along therewith (Table 8).

TABLE 8

Stability of lyophilized formulations having different water contents of drug solutions before freezing, after suspending in iodine addition product of the ethyl ester of the fatty acids of poppyseed oil

| Formulation | Freezing conditions | Water content [mg/mL] of drug solution before freezing | Uniformity of suspension and lapse of time after suspending | | | |
|---|---|---|---|---|---|---|
| | | | 1 hr | 3 hr | 6 hr | 24 hr |
| 20 mg formulation | −40° C. freezing | 1.0 | uniform | uniform | uniform | uniform |
| | | 1.5 | uniform | uniform | uniform | uniform |
| | | 2.0 | uniform | uniform | uniform | uniform |
| | | 3.0 | uniform | uniform | uniform | uniform |
| | | 4.0 | uniform | uniform | uniform | uniform |
| | | 5.1 | uniform | uniform | uniform | uniform |
| | | 6.2 | uniform | uniform | uniform | uniform |
| 80 mg formulation | | 1.0 | uniform | uniform | uniform | uniform |
| | | 1.5 | uniform | uniform | uniform | uniform |
| | | 2.0 | uniform | uniform | uniform | uniform |
| | | 3.0 | uniform | uniform | uniform | uniform |
| | | 4.0 | uniform | uniform | uniform | two layer separation |
| | | 6.2 | uniform | uniform | two layer separation | two layer separation |
| | freezing by gradually cooling from 30° C. to −40° C. over 4 hr | 1.0 | uniform | uniform | uniform | uniform |
| | | 1.5 | uniform | uniform | uniform | uniform |
| | | 2.0 | uniform | uniform | uniform | two layer separation |
| | | 3.0 | uniform | uniform | two layer separation | two layer separation |
| | | 4.0 | uniform | two layer separation | two layer separation | two layer separation |
| | | 6.2 | uniform | two layer separation | two layer separation | two layer separation |

Experimental Example 3-3

The 20 mg formulations and 80 mg formulations obtained in Experimental Example 3 were evaluated for the ability to remain stable as uniform suspensions after suspending in an Experimental Example 3-4

The 20 mg formulations and 80 mg formulations obtained in Experimental Example 3 were compared for suspendability in an iodine addition product of the ethyl ester of the fatty acids of poppyseed oil by the same method as in Experimental Example 2. As a result, as the water content before freezing increased, the suspendability became poor, and the suspendability became poor from lower water content in the 80 mg formulations than in the 20 mg formulations. However, under −40° C. freezing conditions, suspendability was fine even when the water content was high, as compared to the conditions comprising gradually cooling from 30° C. to −40° C. to allow for freezing (Table 9).

TABLE 9

Suspendability of lyophilized formulations having different water contents of drug solutions before freezing in iodine addition product of the ethyl ester of the fatty acids of poppyseed oil

| Formulation | Freezing conditions | Water content [mg/mL] of drug solution before freezing | Suspendability |
| --- | --- | --- | --- |
| 20 mg formulation | −40° C. freezing | 1.5 | easy |
| | | 3.5 | easy |
| | | 5.0 | easy |
| | | 6.0 | easy |
| 80 mg formulation | | 1.6 | easy |
| | | 3.6 | easy |
| | | 5.0 | easy |
| | | 6.2 | slightly difficult |
| | freezing by gradually cooling from 30° C. to −40° C. over 4 hr | 1.6 | easy |
| | | 3.6 | slightly difficult |
| | | 5.0 | slightly difficult |
| | | 6.2 | slightly difficult |

From the above results, for a formulation that does not show easy increase in the viscosity after suspending, does not easily break into two layers after suspending, shows fine suspendability and is easy to handle, the particle distribution and particle shape of the active component particles after lyophilization need to be controlled. The ranges to be controlled are a D90% value of not more than about 40 μm for particle distribution with the highest frequency particle fraction of 3-25 μm, and other than amorphous particles for the particle shape. For particle shape, when the surface of the spherical particles starts to grow into needles, frequency of two layer separation and difficulty in suspendability increase. For the level of needling of the particle shape, the 90% value is preferably set to not more than about 40 μm.

Experimental Example 4

Figure 13:
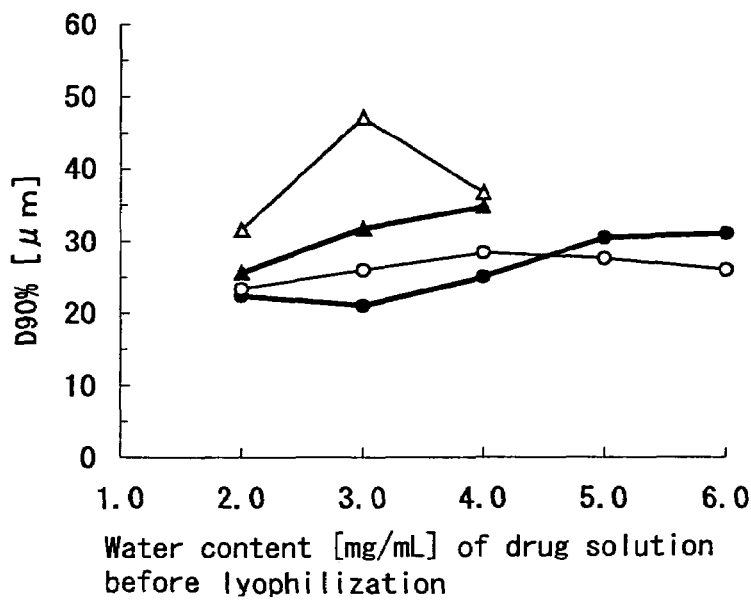
FIG. 13 includes drawings showing the relationship between freezing conditions and the presence or absence of filtration treatment and the particle distribution of the lyophilized formulations, in Experimental Example 4.
Figure 13:
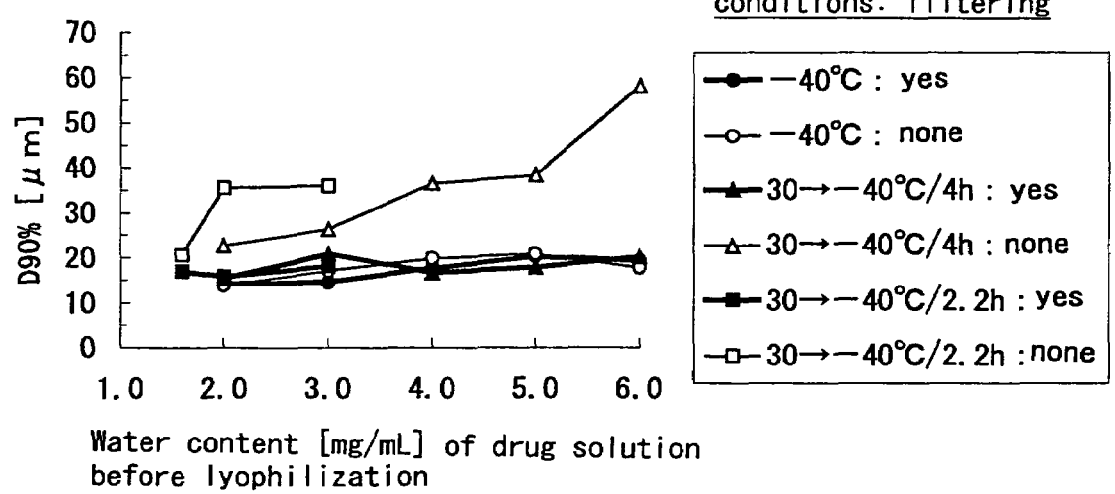

Drug solutions having a water content of about 1.5-about 6 mg/mL were prepared and the solutions filtered for sterilization through a 0.2 μm filter and the solutions free of filtering were frozen under various conditions and lyophilized to give 20 mg formulations and 80 mg formulations. Then the effects of the sterile filtration on the particle distribution were compared. The results are shown in FIG. 13. The drug solutions before sterile filtration were colorless and transparent.

The D90% value changed due to the sterile filtration. When the water content was the same, sterile filtration decreased the D90% value. This difference was found more remarkably under the freezing conditions of charging at 30° C. and cooling to −40° C. in about 2.2 hr (30° C.→−40° C./2.2 h) or charging at 30° C. and cooling to −40° C. in 4 hr (30° C.→−40° C./4 h).

Figure 14:
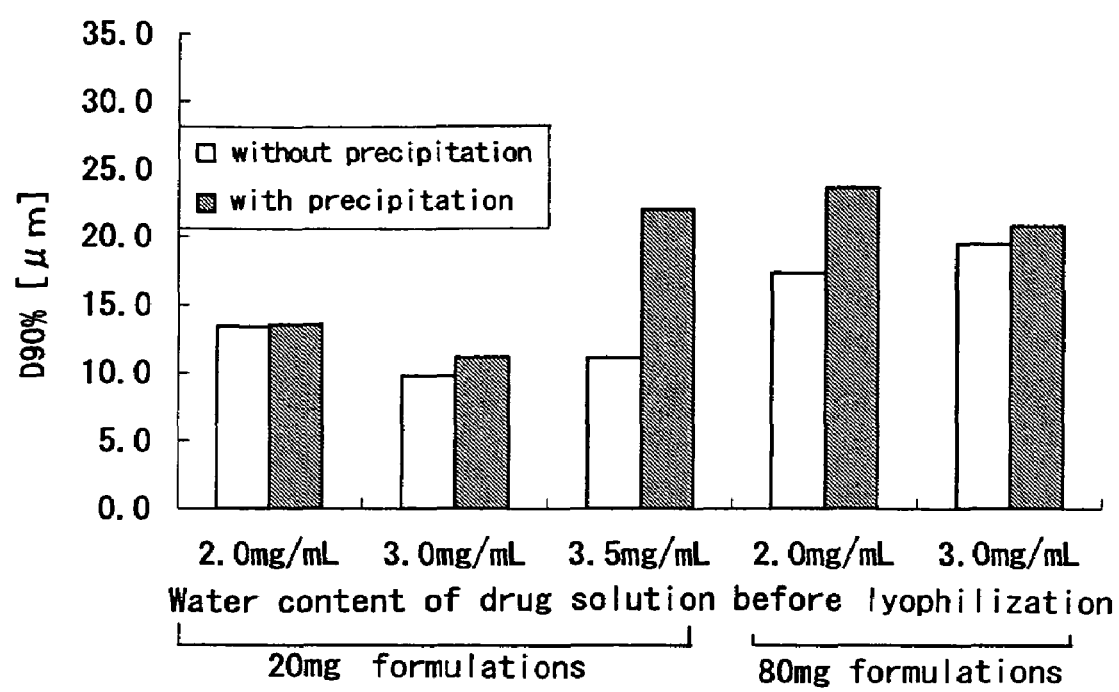
FIG. 14 is a drawing showing the relationship between the addition of a precipitated powder of the main ingredient and the water contents of drug solutions, and D90% values in Experimental Example 4.

Then the drug solutions having a water content of about 2-about 3.5 mg/mL were sterilized by filtration, the active ingredient powder precipitated separately from the drug solution was added in a small amount, the mixture was frozen at −40° C. and 20 mg formulations and 80 mg formulations were prepared using a lyophilizer produced by Kyowa Vacuum Engineering. The obtained lyophilized formulations were examined for the effect of the addition of the active ingredient precipitated powder on the particle distribution and particle shape. The results are shown in FIG. 14. When the active ingredient powder was added, both 20 mg formulations and 80 mg formulations showed slightly increased D90% values at any water content. While the particle shape showed a slight amount of amorphous powder that seemed like the active ingredient powder, the particles were spherical and corresponding to the level of D90% values and showed no clear changes.

Example 5

Figure 15:
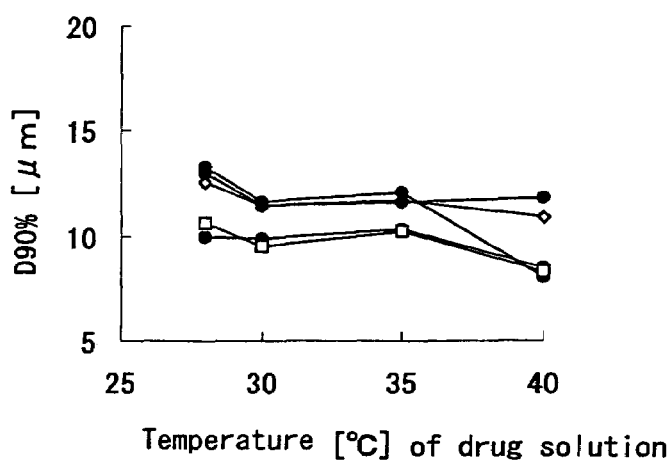
FIG. 15 includes drawings showing the effects due to different temperatures of drug solutions before freezing on the D90% values in Example 5.
Figure 15:
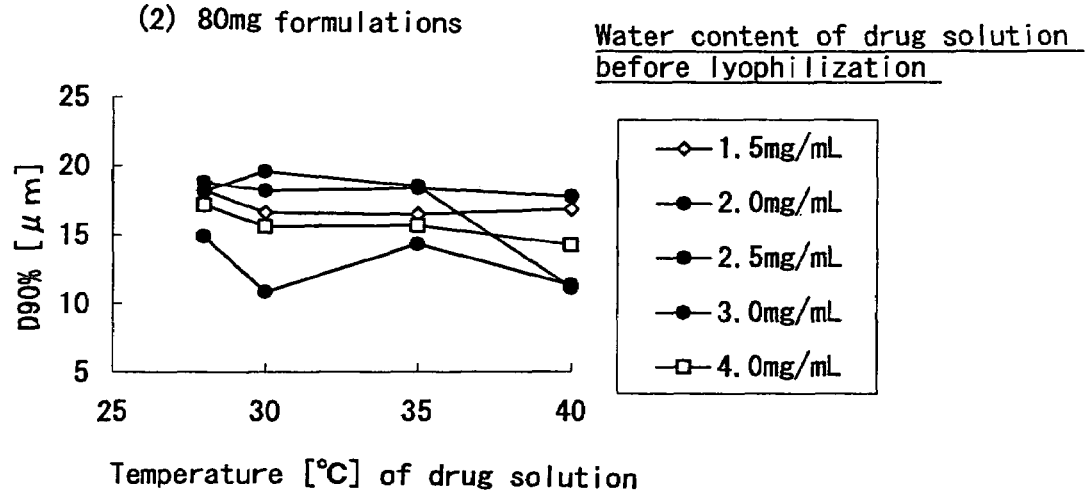
Figure 16:
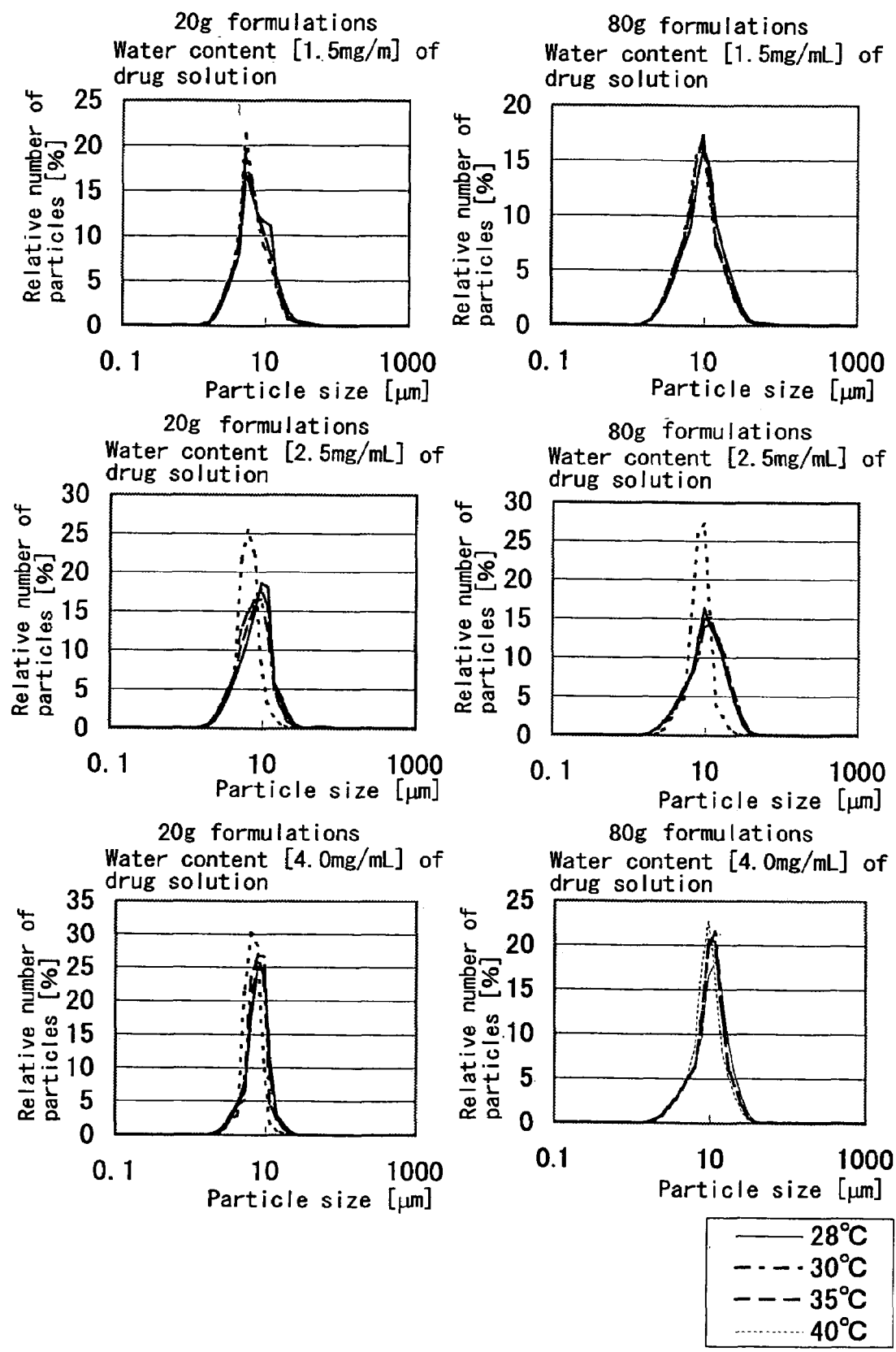
FIG. 16 includes drawings showing the effect caused by different temperatures of drug solutions before freezing on the particle size distribution profile in Example 5.
Figure 17:
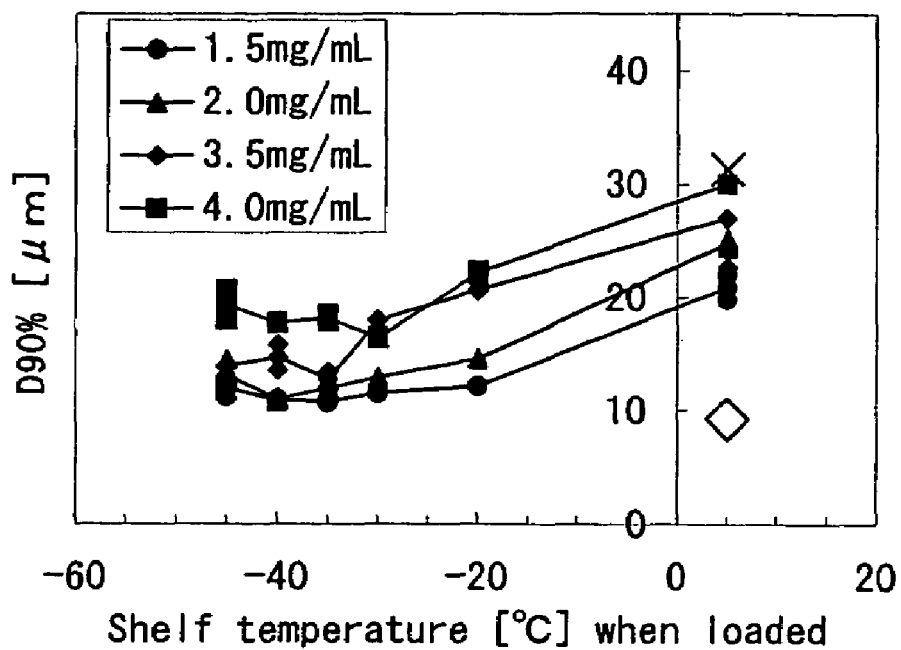
FIG. 17 includes drawings showing the relationship between shelf temperature upon loading and the particle distribution of the lyophilized formulations in Example 6.
Figure 17:
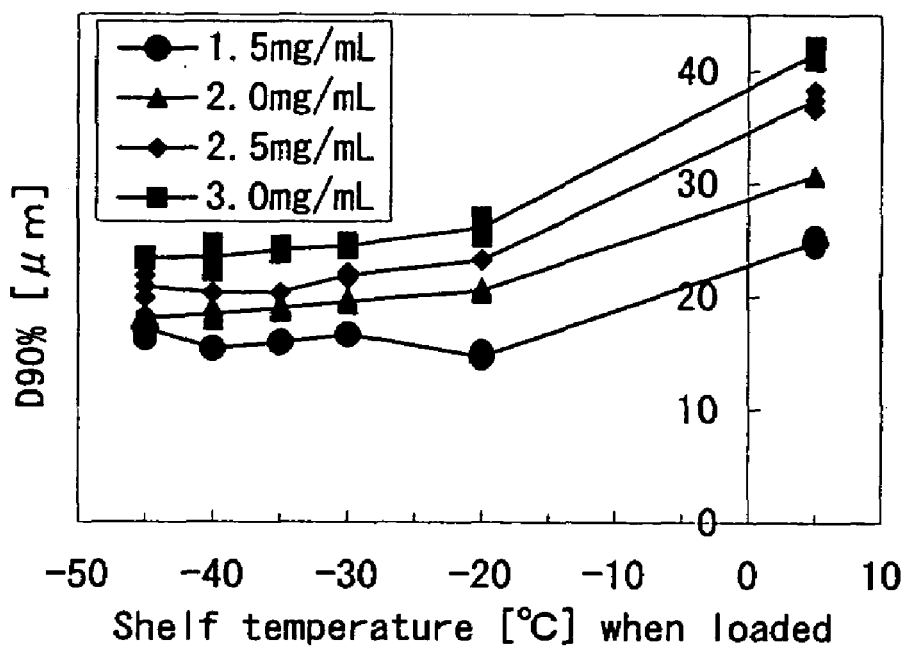
Figure 18:
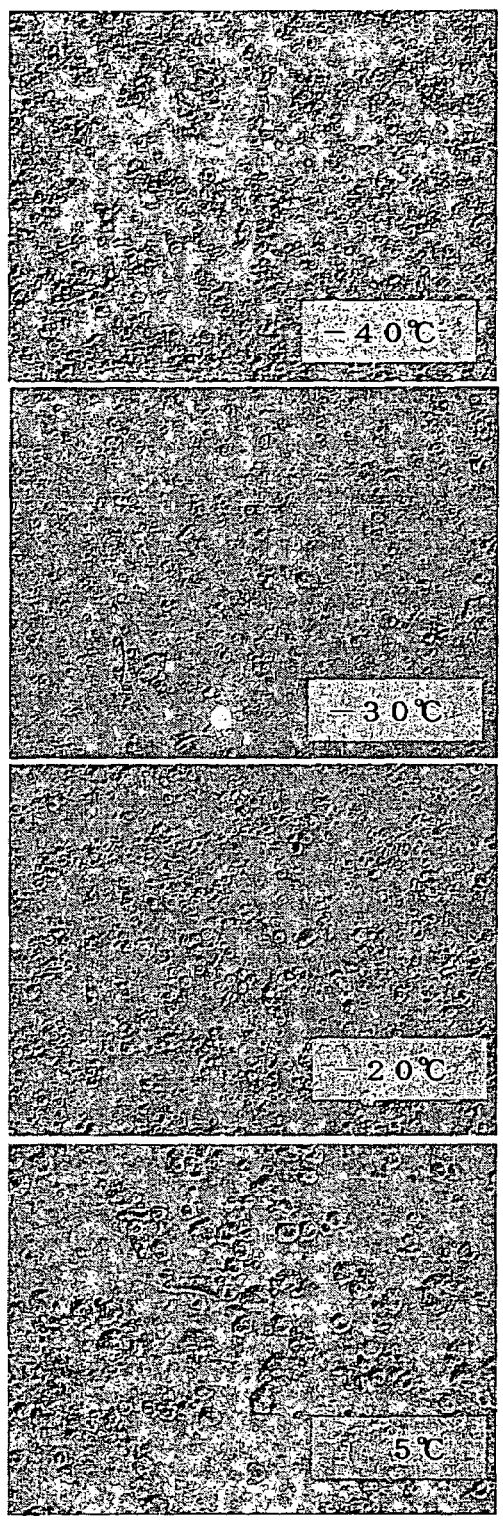
FIG. 18 shows outputs of differential interference microscopic observation of lyophilized formulations at different shelf temperatures upon loading in Example 6.
Figure 18:
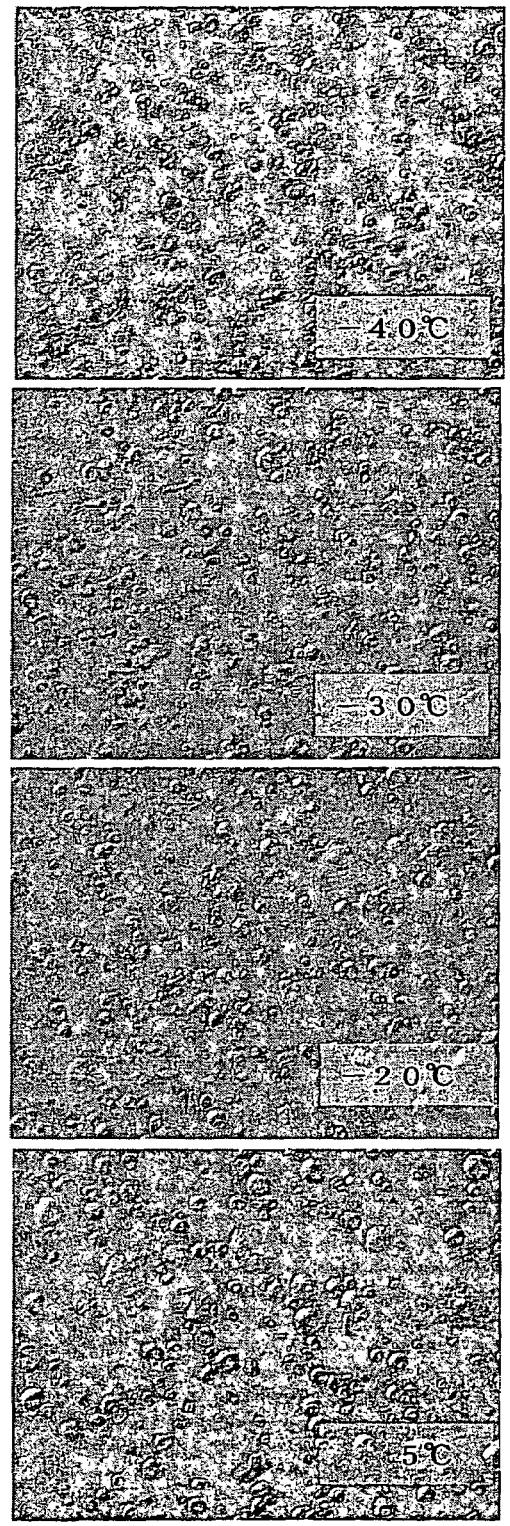
Figure 19:
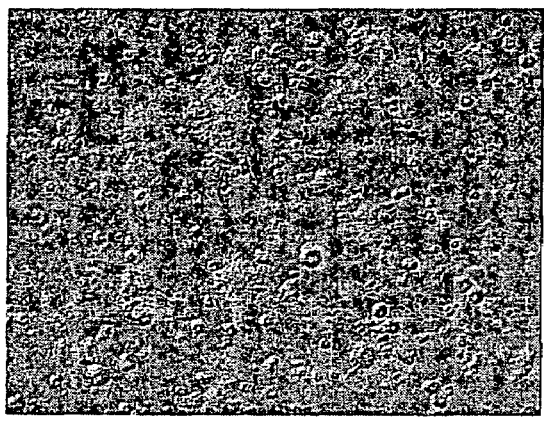
FIG. 19 shows outputs of differential interference microscopic observation of lyophilized formulations frozen on a shelf at 5° C. in Example 6.
Figure 19:
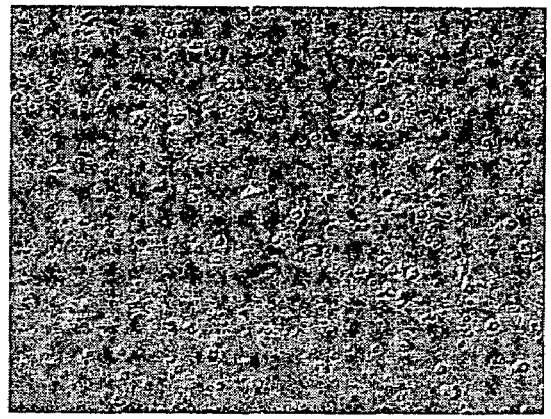

Under −40° C. freezing conditions, there was a fear that variations in the temperature of the drug solution during loading in a lyophilizer might cause changes in the freezing speed, and the particle distributions might become inconsistent between lots or within a lot. Therefore, after adjusting to the water content of about 1.5-about 4.0 mg/mL and sterile filtration, the temperature of the drug solutions was changed in the range of about 28° C.-about 40° C., frozen to −40° C. and the effect on the particle distribution after lyophilization was examined. The results are shown in FIG. 15 and FIG. 16. As a result, as the temperature of the drug solution before freezing increased, the D90% value became smaller and the particle size distribution also became sharp. Therefore, by controlling the liquid formulation temperature (about 35-about 40° C.) and the temperature (about 30° C.) of the filling environment, and preventing a rapid fall of the temperature of the drug solution during loading, the effect on the particle distribution became small.

Example 6

When the manufacturing scale became large and vials were placed one after another on the shelf in the lyophilizer, the shelf temperature set to −40° C. rises by the heat from the drug solution. Depending on the performance of the lyophilizer, the controllable range of −40° C. also varies. From the aspects of optimization of production conditions and selection of equipments for scaling up, the tolerable range of shelf temperature under −40° C. freezing conditions was examined. The water content of drug solutions was adjusted to about 1.5-about 4.0 mg/mL, the drug solutions were sterilized by filtration, charge, frozen and lyophilized at a shelf temperature of 5° C.-−45° C. to give 20 mg formulations and 80 mg formulations. The particle distribution and particle shape of the obtained formulations were evaluated by the aforementioned methods and the effect due to different shelf temperatures upon charging was considered. The results are shown in FIG. 17, FIG. 18 and FIG. 19. When the shelf temperature upon loading was not less than −20° C., both the 20 mg formulations and 80 mg formulations showed greater D90% values as the shelf temperature increased upon charging. However, when the drug solutions were frozen at a shelf temperature of −45° C.-−20° C., the D90% value could be controlled to about 30 μm.

When the shelf temperature upon loading was 5° C., the D90% value became large and the D90% value could be controlled to about 40 μm only in a narrow range of water content. With regard to the particle shape, too, the particle surface was acknowledged to have become needles even at a lower water content, as compared to the shelf temperature of not more than −20° C. The 20 mg formulations having a water content of the drug solution before lyophilization of about 4.0 mg/mL were classified into vials that started to freeze from the bottom of the vial in several minutes after charging at 5° C., and vials that were instantaneously frozen after the lapse of about 30 min after charging. The D90% value of the former (plot x in FIG. 17) was about 30 µm and the particle had a needle surface. The D90% value of the latter (plot ◇ in FIG. 17) was as small as about 10 µm and they were about 10 µm spherical particles.

Experimental Example 7

A method for dissolving cis[((1R,2R)-1,2-cyclohexanediamine-N,N')bis(tetradecanoyloxy)]platinum(II) monohydrate (hereinafter to be also referred to as a bulk) in 2-methyl-2-propanol was considered.

Then, whether the content and analogous substance are affected by stirring in a homomixer was considered. To cis[((1R,2R)-1,2-cyclohexanediamine-N,N')bis(tetradecanoyloxy)]platinum(II) monohydrate was added 2-methyl-2-propanol to a liquid formulation concentration of about 4.0 mg/mL. This was prepared in two Erlenmeyer flasks. One Erlenmeyer flask was stirred with a stirrer at a liquid temperature of about 40° C. after ultrasonication. The other Erlenmeyer flask was stirred at about 10000 rpm at a liquid temperature of about 40° C. using Polytron pulverizer (pulverization diameter G8) manufactured by IKA that pulverizes and dissolves by the same mechanism as a homogenizer. The stirring was continued with the time point when the bulk was dissolved as 0 hr. The drug solution was sampled with the lapse of time and the dissolution state was observed and the content and analogous substances were measured. As a result, black foreign substances and the like were not found by any stirring method, and the content and analogous substances showed no change, as summarized in Table 10.

TABLE 10

Comparison of quality between stirring and dissolution by Polytron and stirring and dissolution by a stirrer

| | Sample | | | | | | | | | | | |
|---|---|---|---|---|---|---|---|---|---|---|---|---|
| | Dissolution | | Content | | Other impurities | | | | | | | |
| Exp. No | stirring method | Stirring time | [vs. 0 h %] | Impurity 1 4.7 min | 7.6 min | 9.2 min | 10.1 min | 14.0 min | 16.6 min | 17.9 min | 23.6 min | 27.9 min |
| 1 | Polytron | 0 | 100 | 0.17 | 0.02 | <0.01 | 0.05 | 0.04 | 0.05 | 0.03 | 0.01 | <0.01 |
| | stirrer | | 100 | 0.17 | 0.02 | <0.01 | 0.05 | 0.04 | 0.05 | 0.03 | 0.01 | <0.01 |
| | Polytron | 0.5 h | 99.5 | 0.17 | 0.02 | <0.01 | 0.04 | 0.04 | 0.04 | 0.04 | <0.01 | 0.02 |
| | stirrer | | 100.9 | 0.18 | 0.03 | <0.01 | 0.05 | 0.04 | 0.04 | 0.01 | <0.01 | 0.01 |
| | Polytron | 1 h | 99.4 | 0.18 | 0.02 | 0.01 | 0.04 | 0.04 | 0.04 | 0.03 | <0.01 | 0.02 |
| | stirrer | | 100.2 | 0.18 | 0.01 | <0.01 | 0.05 | 0.04 | 0.04 | 0.02 | <0.01 | 0.01 |
| | Polytron | 2 h | 100.9 | 0.17 | 0.03 | 0.01 | 0.04 | 0.05 | 0.03 | 0.02 | <0.01 | 0.02 |
| | stirrer | | 103.1 | 0.17 | 0.02 | <0.01 | 0.04 | 0.04 | 0.04 | 0.04 | <0.01 | 0.01 |
| 2 | Polytron | 0 | NP | 0.12 | 0.02 | <0.01 | 0.04 | 0.04 | 0.04 | 0.04 | 0.01 | 0.01 |
| | | 2 h | NP | 0.11 | 0.02 | 0.01 | 0.06 | 0.04 | 0.05 | 0.04 | <0.01 | 0.01 |
| | | 3 h | NP | 0.11 | 0.01 | <0.01 | 0.05 | 0.04 | 0.04 | 0.02 | 0.01 | 0.01 |
| | stirrer | 3 h | NP | 0.17 | 0.03 | 0.01 | 0.05 | 0.04 | 0.04 | 0.01 | <0.01 | 0.02 |

NP: not conducted
(unit %)

A method for preparing a high concentration suspension of a finely divided bulk in a homogenizer and dissolving same by adding 2-methyl-2-propanol to a liquid formulation concentration was considered. To cis[((1R,2R)-1,2-cyclohexanediamine-N,N')bis(tetradecanoyloxy)]platinum(II) monohydrate was added 2-methyl-2-propanol to a concentration of about 80 mg/mL (about 20 times the liquid formulation concentration), and the mixture was pulverized and suspended at about 5000-about 10000 rpm for about 10 min using T.K. ROBOMICS manufactured by TOKUSHU KIKA KOGYO CO., LTD. Thereto was added 2-methyl-2-propanol to the liquid formulation concentration of about 4.0 mg/mL, and the mixture was stirred with a magnetic stirrer. The temperature of the drug solution during the operation was maintained at about 35-about 40° C. and complete dissolution of the bulk was confirmed. As a result, it was acknowledged that, by this operation, the active component could be dissolved in a shorter time than by a conventional dissolution method (after ultrasonication suspending, stirring with a magnetic stirrer), and black foreign substances due to the decomposition of the active component and the like were not generated.

Example 8

Lyophilizing conditions satisfying both the prevention of scattering of formulation during lyophilization and shortening of lyophilizing step were considered.

A 18 mL vial (corresponding to 20 mg formulation) filled with a drug solution (5 mL) and halfway sealed and a 30 mL vial (corresponding to 80 mg formulation) filled with a drug solution (20 mL) and halfway sealed were placed in a lyophilizer, frozen and primarily dried at various degrees of vacuum and shelf temperatures. Simultaneously, a blank solution (2-methyl-2-propanol) was also filled in the same manner and primarily lyophilized, so that the sublimation state could be monitored from an observation window in the lyophilizer. After confirmation of the absence of sublimation of the entire blank solution from the observation window in the lyophilizer, secondary lyophilizing was performed (reaching the degree of vacuum of about 1.0 Torr in one hr and thereafter lyophilizing at a shelf temperature of 40° C. for 6 hr). After completion of the secondary lyophilizing, the vials were sealed and the scattering state was observed.

What affects the sublimation speed in the drying step is the product temperature. What affects the product temperature is the shelf temperature and the degree of vacuum. The product temperature at the sublimation interface of a sample depends on the degree of vacuum, and theoretical product temperature and theoretical vapor pressure can be calculated from the Antoine Equation. However, the freezing phase under the sublimation interface of a sample is affected by the supply of heat from the shelf temperature and becomes higher as it gets closer to the bottom of the vial. The greater the difference in the product temperature between the freezing phase, the greater the sublimation speed becomes. Conversely, scattering tends to occur because the power of sublimation on the bottom of the vial bumps to push up the sublimation face on the upper part of the vial. Therefore, the shelf temperature and degree of vacuum were variously changed so that the difference between the theoretical product temperature at the sublimation interface and shelf temperature (similar to product temperature near bottom of vial) would not become too great. The sublimation speed and scattering degree of the active component then were visually confirmed and the evaluation results are summarized in Table 11. The "scattering level" was divided into three levels of "scattered on vial shoulder by close observation" (level A), "greater scattering on vial shoulder than level A" (level B), "attachment of the active component due to scattering is acknowledged not only on vial shoulder but on the reverse face of halfway-applied rubber seal" (level C).

formulations and not less than 65 hrs for 80 mg formulations". For transition to secondary lyophilizing, not less than 1 hr was spent to gradually reach high vacuum from 0.1 to 1 Torr and the shelf temperature was raised to 40° C., because rapid changes in the degree of vacuum cause scattering of the active component due to turbulence.

Experimental Example 9

To cis[((1R,2R)-1,2-cyclohexanediamine-N,N')bis(tetradecanoyloxy)]platinum(II) monohydrate (bulk) was added 2-methyl-2-propanol to make the concentration about 4.0 mg/mL and after ultrasonication, the mixture was completely dissolved by stirring with heating to about 30° C.-about 40° C. By stepwise addition of water to the solution, several kinds of solutions having a water content in the range of about 1.5-about 6.0 mg/mL were prepared and each solution was stirred to give a homogeneous solution. Then the solution was placed in a pressure tank and sterilized by filtration in an air tight system by nitrogen pressurization (pressure: not more than 1 kg/cm$^2$) using a filter having a pore size of 0.2 μm. The filtrate (17.5 mL) was filled in a vial under a low humidity environment (environment temperature: 28-35° C., relative humidity: 5-40%) while preventing moisture absorption. After the vial was

TABLE 11

Scattering level under each primary drying conditions and necessary primary lyophilizing time

| Primary drying conditions | | Theoretical product temperature | | | Necessary primary drying time | |
|---|---|---|---|---|---|---|
| Degree of vacuum [Torr] | Shelf temperature [° C.] | [° C.]$^{1)}$ at sublimation interface | Difference [° C.]$^{2)}$ (a − b) | Scattering level | [hour]$^{3)}$ 20 mg formulation | 80 mg formulation |
| 5 | 10 | −1.8 | 11.8 | C | NP | <24 |
|   | 5  |      | 6.8  | B | NP | <24 |
|   | 0  |      | 1.8  | A | (12<) <28 | (40<) <58 |
|   | −1 |      | 0.8  | A | (12<) <28 | (40<) <58 |
| 2 | −10 | −12.5 | 2.5 | A | NP | NP |
| 1.5 |    | −15.9 | 5.9 | B | NP | NP |
| 1 |      | −20.7 | 10.7 | C | NP | NP |
| 0.85 | −20 | −22.6 | 2.6 | A | 73 | 140 |

$^{1)}$Theoretical approximation line is an approximation line from 3 points showing the relationship between saturation vapor pressure and product temperature in the following FIGURE as calculated for 2-methyl-2-propanol by Antoine Equation. Based on this line, the intersection with the theoretical approximation line at each degree of vacuum was taken as the theoretical product temperature at the sublimation interface.
$^{2)}$It was assumed that the product temperature near vial bottom was similar to the shelf temperature, and the difference from the theoretical product temperature at the sublimation interface was calculated and taken as a barometer of the sublimation speed.
$^{3)}$The time when the residue of 2-methyl-2-propanol in the vial was not visually observed. However, current conditions essentially require additional lyophilizing step.

The results show that the larger the difference between the theoretical product temperature at the sublimation surface and the shelf temperature was, the larger the amount of scattering became at a visual observation level. Particularly, scattering tended to occur more easily in high vacuum and scattering occurred more easily at 1 Torr than 5 Torr. From the above results and in view of the balance between prevention of scattering and shortened drying time, the primary lyophilizing was effective at "shelf temperature; −1° C., degree of vacuum; 5 Torr" and the primary lyophilizing time was allowed to be "not less than 35 hrs for 20 mg halfway stoppered, the vial was immediately placed on a shelf of a lyophilizer at a shelf temperature of −40° C. to allow for freezing over 10-20 min. Lyophilization was performed (initial exhaustion: shelf temperature −40° C., primary drying conditions: shelf temperature −1° C., degree of vacuum 5 Torr, secondary drying conditions: shelf temperature 40° C., degree of vacuum 1 Torr) to give a cis[((1R, 2R)-1,2-cyclohexanediamine-N,N')bis(tetradecanoyloxy)] platinum(II) lyophilized formulation for 70 mg injection.

Figure 20:
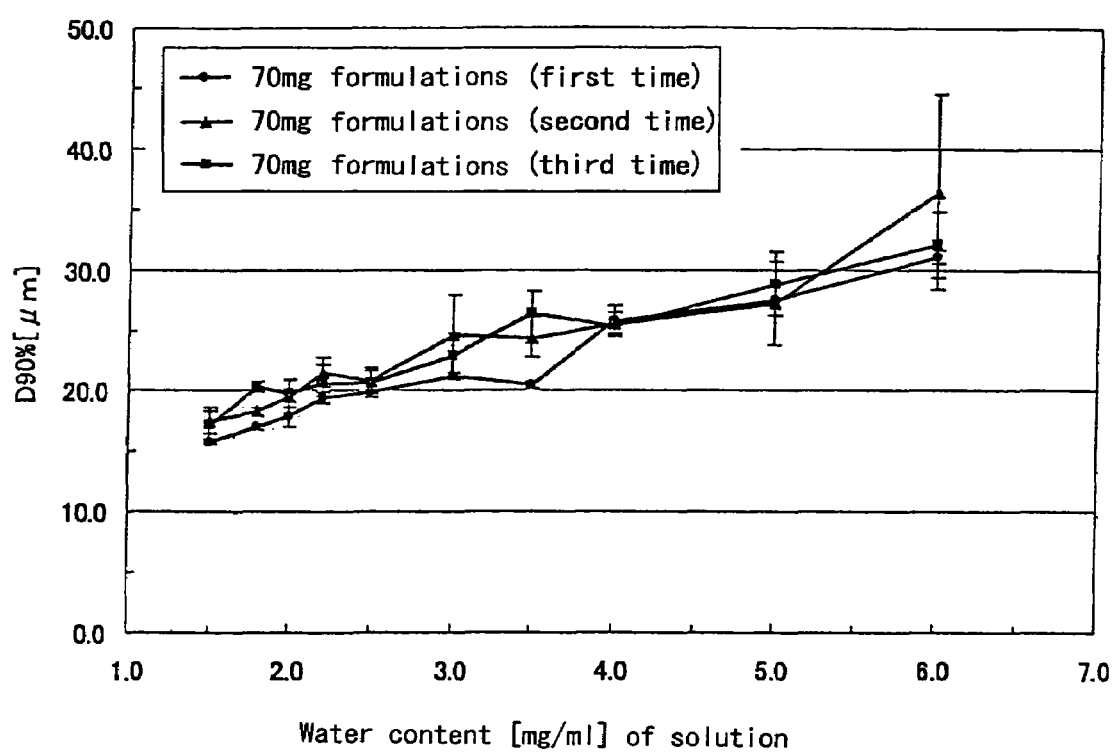
FIG. 20 is a drawing showing the relationship between the water content of drug solutions of 70 mg formulations and freezing conditions, and D90% values, in Example 9.
Figure 21:
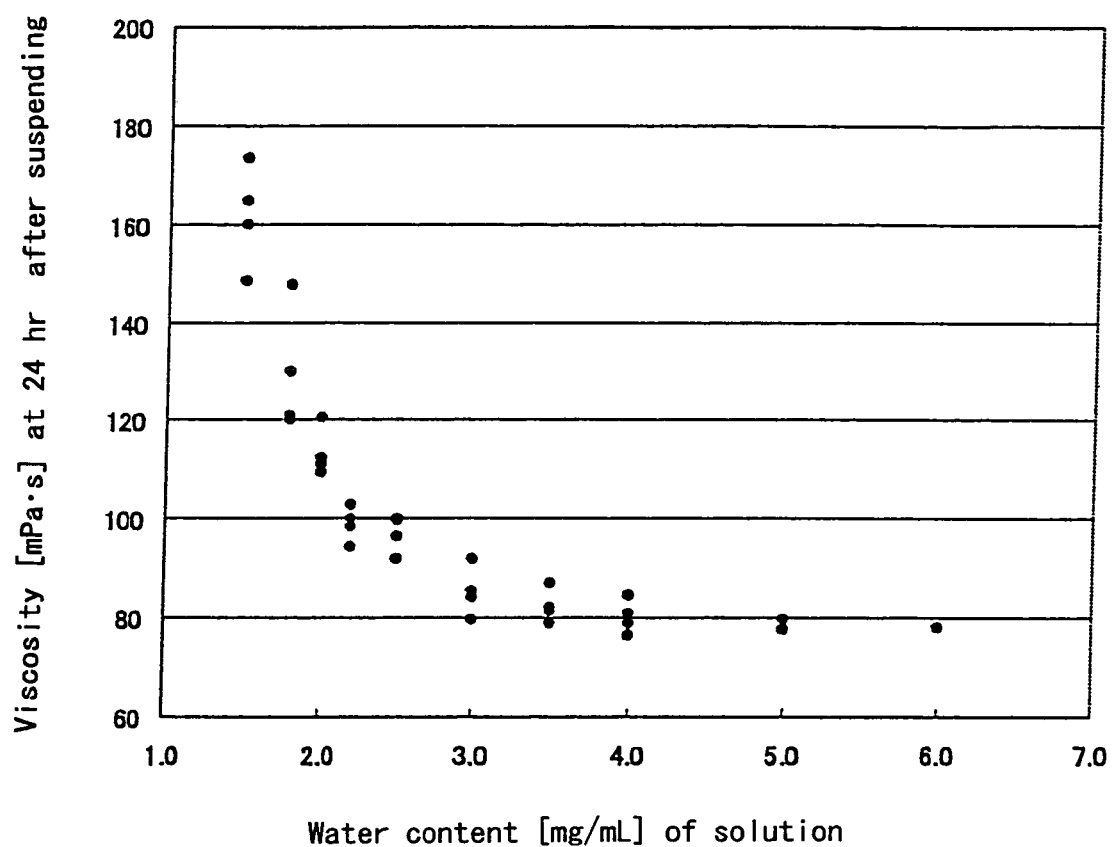
FIG. 21 is a drawing showing water contents of drug solutions of 70 mg formulations before freezing, and viscosity at 24 hrs after suspending in an iodine addition product of the ethyl ester of the fatty acids of poppyseed oil, in Example 9.

The particle distribution and changes in the viscosity of the lyophilized formulation for 70 mg injection having each water content were measured by the methods described in Experimental Example 1-1 and Experimental Example 1-2. The results are shown in FIG. 20 and FIG. 21.

Test Example

The efficacy of the lyophilized formulation of the present invention (hereinafter to be simply referred to as lyophilized formulation) using a lipiodol suspension in a rat liver cancer hepatic intraarterial administration model was studied.

As the lyophilized formulation, the 20 mg formulation prepared according to the method of Experimental Example 2 was used (freezing conditions: slow cooling conditions (freezing speed: 30° C.→−40° C./about 2 hrs); water content when the vial was loaded: 1.5-2 mg/mL; particle distribution: D90% of not more than 20 μm).

The abbreviation LPD in this Test Example stands for an iodine addition product of the ethyl ester of the fatty acids of poppyseed oil (lipiodol ultra fluid). As this LPD, one available from Mitsui Pharmaceut. Inc. (currently Nihon Schering K.K.) was used.

(Test System)

1) Cells

Rat ascitic liver cancer cell line AH109A provided by Kumamoto University was implanted in the liver of male Donryu rat according to the procedure described under the section of 3) Tumor implantation in the Test method mentioned later, maintained by in vivo passage and used for the test.

2) Rat

Male Donryu rats purchased from Charles River Japan, Inc. were used.

(Test Method)

1) Reagent, Test Solution and Instruments
i) As a general anesthetic, Nembutal injection available from DAINIPPON PHARMACEUTICAL CO., LTD. was used.
ii) As a Hanks solution, Hanks' balanced salt solution available from GIBCO BRL was used.
iii) As an indwelling needle, SurFlow Flash 18G×2" available from TERUMO CORPORATION was used.
iv) As a gelatin sponge for hemostasis, spongel available from Yamanouchi Pharmaceutical Co., Ltd. was used.
v) As a polyethylene tube, polyethylene tube SP10 available from Natume Seisakusyo Co., Ltd. was used.
vi) As a chondroitin sulfate formulation, 1% chondron parenteral injection available from Kaken Pharmaceutical Co., Ltd. was used.
vii) As a heparin-containing physiological saline, one prepared by adding swine-derived heparin, available from GIBCO BRL, to Otsuka Normal Saline available from Otsuka Pharmaceutical Co., Ltd. to 20 U/ml was used.
viii) As electronic calipers, electronic digital calipers MAX-CAL manufactured by Nihon Sokutei Kougu K.K. were used.
ix) As a syringe, a 50 μl micro syringe manufactured by Hamilton was used.

2) Animal Breeding

The breeding environment in the breeding room was temperature of not lower than 20° C. and not higher than 26° C., humidity of not less than 30% and not more than 70%, brightness and darkness cycle of lighting at 8 am and lights-out time at 8 pm, which was 12 hr light period and 12 hr dark period. The feed used was CL-2 available from CLEA JAPAN, INC. Water was fed from a water feeding bottle.

Figure 22:
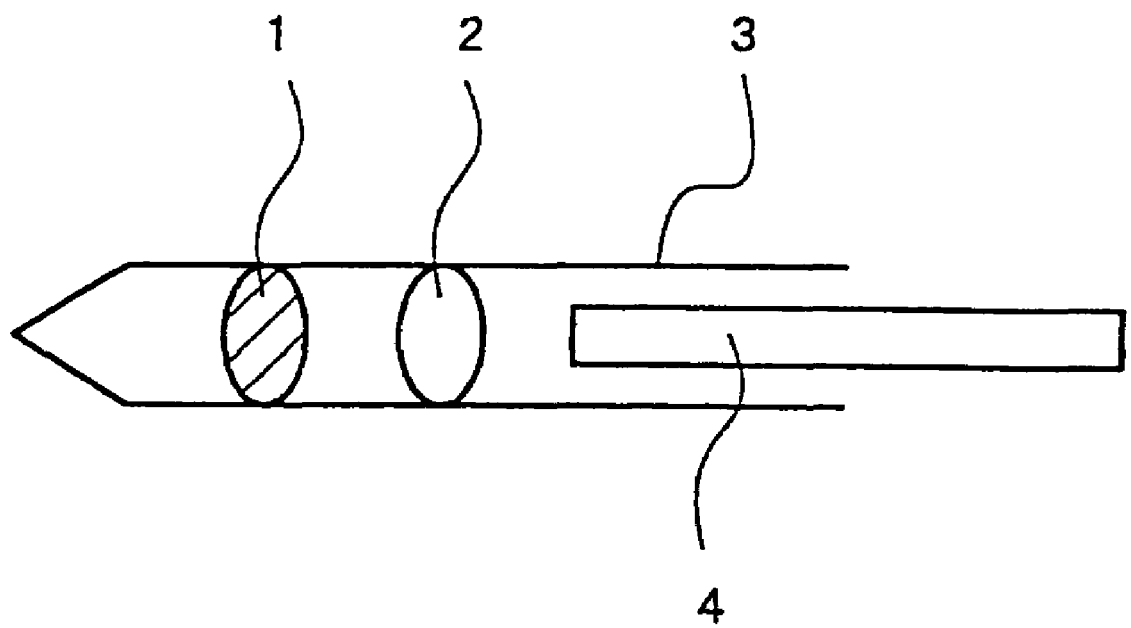
FIG. 22 is a drawing showing a catheter portion of an indwelling needle used in Test Example, wherein symbol 1 shows an implanted tumor fragment, symbol 2 shows a gelatin sponge for hemostasis, symbol 3 shows a catheter portion and symbol 4 shows a polyethylene tube.

3) Tumor Implantation
i) Under general anesthesia, the abdomen of a tumor-bearing rat was opened and a solid tumor mass of AH109A was excised from the liver. The general anesthetic was intraperitoneally administered at about 50 mg/kg. In the following, general anesthesia was always given in the same manner.
ii) The excised tumor mass was cut into small pieces in the Hanks solution with scissors to prepare an about 1 mm square implanted tumor fragment.
iii) Under general anesthesia, the abdomen of a healthy rat was shaved with clippers and opened after disinfecting with Isodine.
iv) Using a catheter portion of an indwelling needle, the implanted tumor fragment prepared in ii) was grafted to the left lobe of the liver. The tip of the catheter portion was cut off at an acute angle with scissors. As shown in FIG. 22, a gelatin sponge 2 for hemostasis cut into a size similar to the implanted tumor fragment 1 and the implanted tumor fragment 1 were set in this order from the tip of the catheter portion 3, and about 1 cm of the tip of the catheter portion 3 was inserted into the liver. The implanted tumor fragment 1 was thrust into the liver with the gelatin sponge 2 from the syringe connection side of the catheter portion 3 using a polyethylene tube 4 and then the catheter portion 3 was drawn out.
v) In order to prevent liver adhesion, a chondroitin sulfate formulation and heparin-containing physiological saline were added intraperitoneally. The amount added of the chondroitin sulfate formulation was 0.1 ml per individual. The heparin-containing physiological saline was added until the entire liver was soaked.
vi) The abdomen was sutured with a silk thread and after disinfecting the suture part with Isodine, the rat was put back in the breeding cage.

4) Formulation of Administration Liquid

An LPD suspension of a lyophilized formulation was prepared at 20 mg/mL.

LPD (1 ml) was added to the lyophilized formulation (20 mg) and suspended to give a homogeneous suspension. This administration liquid was prepared when in use on the administration day and, after formulation, preserved at room temperature until administration.

5) Efficacy Evaluation
i) The abdomen of the rat was shaved after grafting AH109A to the liver and, after breeding for 19 or 20 days, disinfected with Isodine and opened under general anesthesia.
ii) The survival of the tumor was confirmed and, as for the individual with viable tumor, the long axis and the short axis of the tumor were measured with electronic calipers.
iii) The tumor area was calculated from the following formula.

$$\text{Tumor area (mm}^2\text{)} = \text{long axis (mm) of tumor} \times \text{short axis (mm) of tumor.}$$

Tumor-bearing rats having a tumor area of 100-250 mm$^2$ were used.
iv) The test groups included 4 groups of a non-treatment group, a sham operation group, an LPD administration group, and a lyophilized formulation/LPD administration group.

v) The administration route of the pharmaceutical agent was always hepatic intraarterial administration. The hepatic intraarterial administration was performed using a 50 μl micro syringe connected to a polyethylene tube as a catheter. The catheter was inserted from the gastroduodenal artery and fixed so that the tip reached the bifurcation of common hepatic artery and proper hepatic artery and then pharmaceutical agent (20 μl) was administered. After administration of the pharmaceutical agent, the catheter was drawn out from the gastroduodenal artery and the gastroduodenal artery was ligated with a silk thread before and after the catheter insertion site. In the non-treatment group, the abdomen was opened and the tumor diameter was only measured and in the sham operation group, the gastroduodenal artery was only ligated with a silk thread.

vi) After the treatment/administration, the abdomen was sutured with a silk thread and the suture part was disinfected with Isodine and then all the animals were put back in the breeding cages.

vii) After breeding for a week, the abdomen of the animals was opened under general anesthesia.

viii) As described above, the long axis and the short axis of the tumor were measured using electronic calipers.

(Evaluation Method of Results, Statistical Method Used for Analysis)

(1) Calculation of Tumor Growth Rate of Individual

From the following formula, the tumor growth rate was calculated per individual. Tumor growth rate (%)=100 (%)× long axis (mm)×short axis (mm) of tumor one week after administration/long axis (mm)×short axis (mm) of tumor at the time of administration (2) Test Method of Multiple Comparison and Evaluation Method of Efficacy Seven test subjects from each group were evaluated as follows. For each group, the average value and standard deviation of tumor growth rate were calculated. Thereafter, the multiple comparison test shown in the following was performed.

i) Effect of Surgical Operation and LPD on Tumor Growth

For 3 groups of the non-treatment group, sham operation group and LPD administration group, a 2-way type modified Dunnett multiple comparison test was performed with the non-treatment group as a control group. When the sham operation group or the LPD administration group showed a statistically significant difference in the tumor growth rate from the non-treatment group (p value <0.05) and showed a difference in the average value of the tumor growth rate of not less than 25% from the average value of the non-treatment group, the surgical operation itself and LPD were evaluated to affect the tumor growth.

ii) Effectiveness of Pharmaceutical Agent

The two groups of the LPD administration group and lyophilized formulation/LPD administration group were subjected to a 2-way type modified Dunnett multiple comparison test in the same manner as in the above-mentioned i), with the LPD administration group as a control group. For the pharmaceutical agent administration group showing a significantly low (p value <0.05) tumor growth rate, and the average value of the tumor growth rate lower by not less than 25%, as compared to the LPD administration group, the pharmaceutical agent of the group was evaluated to be effective. In addition, for the pharmaceutical agent administration group that showed the average value of the tumor growth rate of less than 100%, the pharmaceutical agents of the group was evaluated to have a tumor regressive effect.

(Results and Discussion)

(1) Effect of Surgical Operation and LPD on Tumor Growth

In the sham operation group, while the average value of tumor growth rate was lower by 11% as compared to the non-treatment group, there was no significant difference between the tumor growth rates of the two groups (p value; 0.9285). In the LPD administration group, the average value of tumor growth rate was lower by 28% as compared to the non-treatment group, but there was no significant difference between the tumor growth rates (p value; 0.6686).

Therefore, it was shown that, in a rat liver cancer hepatic intraarterial administration model using rat ascitic liver cancer cell line AH109A, neither the surgical operation per se to ligate the gastroduodenal artery, which was the administration site, nor the administration of LPD (medium) affected the tumor growth (Table 12).

(2) Effectiveness of the Lyophilized Formulation of the Present Invention

Making the amount of administration liquid constant at 20 μl per individual, and using an LPD suspension prepared to a clinical administration liquid concentration, the effectiveness of the lyophilized formulation was examined in a rat liver cancer hepatic intraarterial administration model with the tumor growth rate one week after the administration as an index.

In all cases of the lyophilized formulation/LPD administration group, the tumor growth rate was less than 100% (Table 12). In the lyophilized formulation/LPD administration group, the average value of the tumor growth rate was lower by 118% as compared to the LPD administration group and the tumor growth rate was significantly low (p value <0.0001).

Therefore, in the rat liver cancer hepatic intraarterial administration model using rat ascitic liver cancer cell line AH109A, the lyophilized formulation of the present invention/LPD was effective, showing a tumor regressive effect.

TABLE 12

| Test group | Tumor growth rate (%) average ± standard deviation | p value 1[a)] | 2[b)] |
|---|---|---|---|
| Non-treatment | 213 ± 29 | | |
| Sham operation | 202 ± 106 | 0.9285 | |
| LPD | 185 ± 37 | 0.6686 | |
| 20 mg/mL lyophilized formulation/LPD | 67 ± 24 | | <0.0001 |

Figure 23:
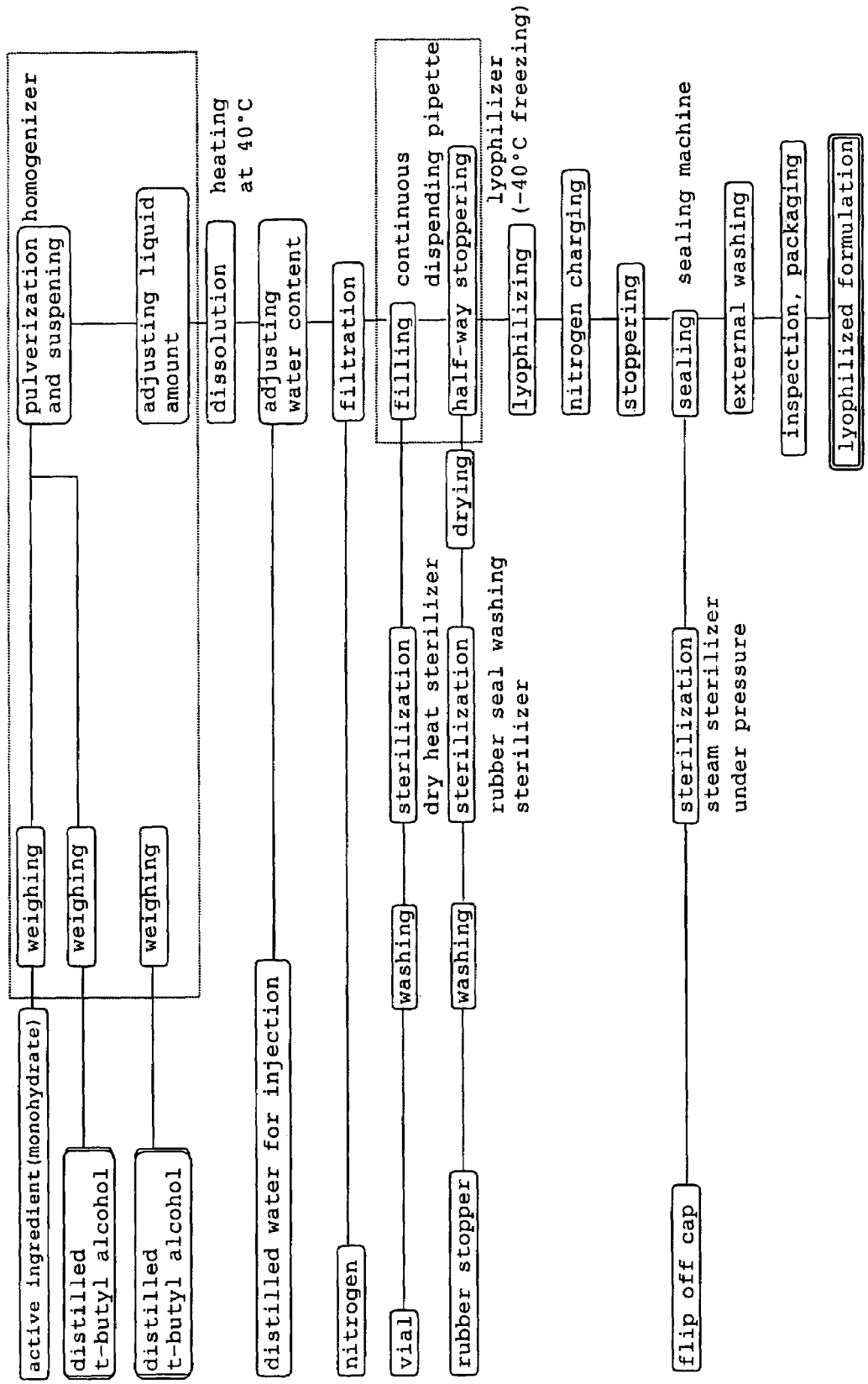
FIG. 23 is an outline of production flow chart of a lyophilized formulation.

Each group n = 7
[a)]Dunnett's multiple comparison test modified in 2-way type with the non-treatment group as a control group
[b)]Dunnett's multiple comparison test modified in 2-way type with the LPD group as a control group
FIG. 23 shows a production flow chart of the lyophilized formulation.

INDUSTRIAL APPLICABILITY

According to the present invention, a lyophilized formulation of cis[((1R,2R)-1,2-cyclohexanediamine-N,N')bis(R$^1$)]platinum(II) has been provided, which does not easily show layer separation and changes in the viscosity with the lapse of time, shows fine suspendability, and which is easy to handle during administration.

This application is based on a patent application No. 290265/2001 filed in Japan, the contents of which are hereby incorporated by reference.

The invention claimed is:

1. A method to produce a lyophilized formulation comprising a cis[((1R,2R)-1,2-cyclohexanediamine-N,N')bis(tetradecanoyloxy)]platinum(II) as a main ingredient, comprising the following steps:

(1) a step of dissolving a cis[(((1R,2R)-1,2-cyclohexanediamine-N,N')bis(tetradecanoyloxy)]platinum(II) in 2-methyl-2-propanol,
(2) a step of adjusting a water content of said solution to 1.0-6.0 mg/mL,
(3) a step of quickly freezing said solution, and
(4) a step of lyophilizing said frozen solution.

* * * * *